US006610702B2

(12) United States Patent
Lehn et al.

(10) Patent No.: US 6,610,702 B2
(45) Date of Patent: Aug. 26, 2003

(54) AMMONIUM SALTS OF INOSITOL HEXAPHOSPHATE, AND USES THEREOF

(75) Inventors: Jean-Marie Lehn, Strasbourg (FR); Yves Claude Nicolau, Newton, MA (US); Stephane P. Vincent, Strasbourg (FR)

(73) Assignee: GMP Oxycell, Inc., Fort Lauderdale, FL (US)

( * ) Notice: Subject to any disclaimer, the term of this patent is extended or adjusted under 35 U.S.C. 154(b) by 0 days.

(21) Appl. No.: 09/920,140

(22) Filed: Aug. 1, 2001

(65) Prior Publication Data

US 2002/0173494 A1 Nov. 21, 2002

Related U.S. Application Data

(60) Provisional application No. 60/222,089, filed on Aug. 1, 2000.

(51) Int. Cl.[7] .................. C07D 453/02; C07D 211/12; C07D 215/06; C07D 209/20; A61K 31/6615
(52) U.S. Cl. .................. 514/305; 514/311; 514/415; 546/133; 546/164; 548/494
(58) Field of Search .................. 546/133, 164; 548/494; 514/305, 311, 415

(56) References Cited

U.S. PATENT DOCUMENTS

| | | | |
|---|---|---|---|
| 3,847,738 A | 11/1974 | Brake et al. | 195/1.8 |
| 4,546,095 A | 10/1985 | Markov | 514/23 |
| 4,699,926 A | 10/1987 | Abraham et al. | 514/563 |
| 4,731,381 A | 3/1988 | Abraham et al. | 514/571 |
| 4,731,473 A | 3/1988 | Abraham et al. | 562/464 |
| 4,751,244 A | 6/1988 | Abraham et al. | 514/563 |
| 4,757,052 A | 7/1988 | Markov | 514/23 |
| 4,849,416 A | 7/1989 | Pendleton et al. | 514/150 |
| 4,861,795 A | 8/1989 | Suh et al. | 514/510 |
| 4,866,052 A | 9/1989 | Hider et al. | 514/184 |
| 4,887,995 A | 12/1989 | Abraham et al. | 604/4 |
| 4,948,582 A | 8/1990 | Suh et al. | 424/529 |
| 5,015,663 A | 5/1991 | Suh et al. | 514/510 |
| 5,039,665 A | 8/1991 | Markov | 514/23 |
| 5,296,466 A | 3/1994 | Kilbourn et al. | 514/6 |
| 5,344,393 A | 9/1994 | Roth et al. | 604/4 |
| 5,428,007 A | 6/1995 | Fisher et al. | 514/6 |
| 5,451,205 A | 9/1995 | Roth et al. | 604/6 |
| 5,612,207 A | 3/1997 | Nicolau et al. | 435/173.6 |
| 5,906,915 A | 5/1999 | Payrat et al. | 435/2 |

FOREIGN PATENT DOCUMENTS

| | | |
|---|---|---|
| EP | 0 146 338 A2 | 6/1985 |
| JP | 51-108020 | 9/1976 |
| JP | 55-147295 | 11/1980 |
| WO | WO 92/20368 | 11/1992 |
| WO | WO 92/20369 | 11/1992 |
| WO | WO 93/16688 | 9/1993 |
| WO | WO 94/21117 | 9/1994 |
| WO | WO 95/03068 | 2/1995 |
| WO | WO97/42819 | 11/1997 |
| WO | WO 01/13933 A2 | 3/2001 |
| WO | WO 01/24830 A2 | 4/2001 |

OTHER PUBLICATIONS

Hirst et al.; "The Modification of Hemoglobin Affinity For Oxygen and Tumor Radiosensivity by Antilipidemic Drugs", Radiation Research 112: 164–172, (1987).

Ogata and McConnell.; "Triphosphate Spin–Label Studies of Allosteric Interactions In Hemoglobin", Annals of the New York Academy of Sciences, 222: 56–67, (Dec. 31, 1973).

Ruckpaul et al.; "Interaction of Hemoglobin with Ions Allosteric Effects of the Binding of Anions", Biochimica et Biophysica Acta 236:211–221, (1971).

Benesch and Benesch; "The Effect of Organic Phosphates From the Human Erythrocyte on the Allosteric Prosperities of Hemoglobin", Biochemical and Biophysical Research Communications, 26 (2): 163–167, (1967).

Lalezari et al.; "New Effectors Of Human Hemoglobin: Structure and Function", Biochemistry 29: 1515–1523, (1990).

Abraham et al.; "Design, Synthesis, and Testing of Potential Antisickling Agents. 1. Halogenated Benzyloxy and Phenoxy acids", J. Med. Chem. 25: 1015–1017, (1982).

Teisseire et al.; "Physiological Effects of High $-P_{50}$ Erythrocyte Trasnfusion on Piglets", Journal of Applied Physiology, 58(4): 1810–1817, (Apr. 1985).

Brooksbank and Balazs; Superoxide Dismutase and Lipoperoxidation in Down's Syndrome Fetal Brain, The Lancet 1: 881–882, (Apr. 16, 1983).

Benesch and Benesch; "Intracellular Organic Phosphates as Regulators of Oxygen Release by Haemoglobin", Nature, 221: 618–622, (Feb. 15, 1969).

Arnone Arthur; "X–ray Diffraction Study of Binding of 2,3–Diphosphoglycerate to Human Deoxyhaemoglobin", Nature 237: 146–149, (May 19, 1972).

Abraham et al.; "Physiological and X–ray Studies of Potential Antisickling Agents", Proc. Natl. Acad. Sci. USA, 80:324–328, (Jan. 1983).

Teisseire et al.; "Long–term Physiological Effects of Enhanced $O_2$ Release by Inositol Hexaphosphate–Loaded Erythrocytes", Proc. Natl. Acad. Sci. USA, 84: 6894–6898, (Oct. 1987).

Lalezari et al.; "LR16, a Compound with Potent Effects on the Oxygen affinity of Hemoglobin, on Blood Cholesterol, and on Low Density Lipoprotein", Proc. Natl. Acad. Sci. USA, 85: 6117–6121, (Aug. 1988).

Bruggemann et al.; "Low Oxygen–Affinity Red Cell Produced In a Large–Volume, Continous–Flow Electroporation System", Tranfusion 35(6): 478–485, (Jun. 1995).

*Primary Examiner*—Mukund J. Shah
*Assistant Examiner*—Hong Liu
(74) *Attorney, Agent, or Firm*—Dana M. Gordon; Foley Hoag LLP

(57) ABSTRACT

The present invention comprises compounds, compositions thereof, and methods capable of delivering inositol hexaphospahte (IHP) to the cytoplasm of mammalian cells. In certain embodiments, the present invention relates to compounds, compositions thereof, and methods that enhance the ability of mammalian red blood cells to deliver oxygen, by delivering IHP to the cytoplasm of the red blood cells.

7 Claims, 20 Drawing Sheets

Figure 1

| Allosteric Effector | Structure or Name |
|---|---|
| ICP6 | Nona-cyclohexylammonium tri-sodium inositol hexaphosphate |
| IC2P1 | Bis-dicyclohexylammonium deca-sodium inositol hexaphosphate |
| IC2P2 | Octa-dicyclohexylammonium inositol hexaphosphate |
| SV42 | Hexa-dibenzylmethylammonium inositol hexaphosphate |
| SV44 | 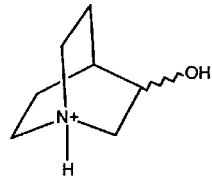 Hepta inositol hexaphosphate |
| SV45 | 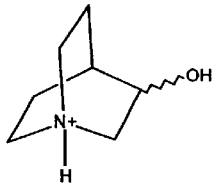 Dodeca- inositol hexaphosphate |
| SV46 | Nona-piperidinium inositol hexaphosphate |

Figure 2

| Allosteric Effector | Structure or Name |
|---|---|
| SV47 | Penta-H₃N-Phe-OMe inositol hexaphosphate |
| SV48 | Nona-H₃N-Phe-OMe inositol hexaphosphate |
| SV51 | Hexa-1-indanylammonium inositol hexaphosphate |
| SV52 | Hepta-  inositol hexaphosphate |
| SV53 | Nona- 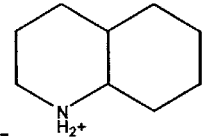 inositol hexaphosphate |
| SV55 | Hepta-H₃N-Phe-OEt inositol hexaphosphate |
| SV56 | Hexa-H₃N-Phe-OEt inositol hexaphosphate |
| SV57 | Octa-H₃N-sec-Leu-Ot-Bu inositol hexaphosphate |
| SV58 | Dodeca-diisopropylammonium inositol hexaphosphate |
| SV59 | Octa-H₂N-Pro-Ot-Bu inositol hexaphosphate |

Figure 3

| Allosteric Effector | Structure or Name |
|---|---|
| SV68 | Deca-$H_3N$-Tyr-OEt inositol hexaphosphate |
| SV71 | Undeca-4-t-butylcyclohexylammonium inositol hexaphosphate |
| SV73 | Tetra-cyclohexyl-1,2-bis-ammonium inositol hexaphosphate |
| SV74 | Undeca-adamantylammonium inositol hexaphosphate |
| SV75 | Nona-cycloheptylammonium inositol hexaphosphate |
| SV78 | Undeca-cyclopentylammonium inositol hexaphosphate |
| SV80 | Hepta-$H_3N$-Try-OEt inositol hexaphosphate |
| SV81 | Undeca-cyclohexylammonium inositol hexaphosphate |
| SV99 | Hexa-dimethylcyclohexylammonium inositol hexaphosphate |
| SV115 | Nona-hexylammonium inositol hexaphosphate |
| SV131 | Undeca-cyclooctanylammonium inositol hexaphosphate |
| SV135 | Nona-octylammonium inositol hexaphosphate |
| IP12 | Hepta-tributylammonium inositol hexaphosphate |

Figure 4

*Cyclic Primary Amines*

| Reference | Counter-cation | Number | Mol. Formula | Mol. Weight (g.mol⁻¹) |
|---|---|---|---|---|
| ICP$_1$ | | 1 Bu$_3$NH$^+$ 6 CyNH$_3^+$ 5 Na$^+$ | C$_{54}$H$_{118}$O$_{24}$N$_7$P$_6$Na$_5$ | 1550.37 |
| ICP$_2$ | | 9 CyNH$_3^+$ 3 Na$^+$ | C$_{60}$H$_{130}$O$_{24}$N$_9$P$_6$Na$_3$ | 1616.57 |
| ICP$_3$ | CyNH$_3^+$ | 9 CyNH$_3^+$ 3 Na$^+$ | C$_{60}$H$_{130}$O$_{24}$N$_9$P$_6$Na$_3$ | 1616.57 |
| ICP$_4$ | | 11 CyNH$_3^+$ 1 Na$^+$ | C$_{72}$H$_{160}$O$_{24}$N$_{11}$P$_6$Na$_1$ | 1772.97 |
| ICP$_5$ | | 9 CyNH$_3^+$ 3 Na$^+$ | C$_{60}$H$_{130}$O$_{24}$N$_9$P$_6$Na$_3$ | 1616.57 |
| ICP$_6$ | | 9 CyNH$_3^+$ 3 Na$^+$ | C$_{60}$H$_{130}$O$_{24}$N$_9$P$_6$Na$_3$ | 1616.57 |
| SV52 | NoNH$_3^+$ | 7 No-NH$_3^+$ | C$_{55}$H$_{104}$O$_{24}$N$_7$P$_6$ | 1433.32 |
| SV51 | IndNH$_3^+$ | 6 Ind-NH$_3^+$ | C$_{60}$H$_{84}$O$_{24}$N$_6$P$_6$ | 1459.21 H$_{5.80}$ N$_{5.76}$ C$_{49..39}$ |
| SV69 | tBuCyNH$_3^+$ | 11 tBuCy-NH$_3^+$ | C$_{116}$H$_{249}$O$_{24}$N$_{11}$P$_6$ | 2368.18 H$_{10.6}$C$_{58.83}$N$_{6.51}$ |
| SV71 | | 7 tBuCy-NH$_3^+$ | C$_{76}$H$_{165}$O$_{40}$N$_8$P$_6$ | 1747.03 H$_{9.52}$C$_{52.26}$N$_{5.61}$ |
| SV74 | Ad-NH$_3^+$ | 11 Ad-NH$_3^+$ | C$_{116}$H$_{194}$O$_{24}$N$_{11}$P$_6$ | 2312.74 H$_{8.46}$C$_{60.24}$N$_{6.66}$ |
| SV75 | ChNH$_3^+$ | 9 Ch-NH$_3^+$ | C$_{69}$H$_{153}$O$_{24}$N$_9$P$_6$ | 1819.52 H$_{5.98}$ C$_{47.53}$ N$_{4.62}$ |
| SV76 | CpNH$_3^+$ | 11 Cp-NH$_3^+$ | C$_{61}$H$_{139}$O$_{24}$N$_{11}$P$_6$ | 1596.69 H$_{8.77}$C$_{45.89}$N$_{9.65}$ |
| SV131 | | 11 Co-NH$_3^+$ | C$_{94}$H$_{205}$O$_{24}$N$_{11}$P$_6$ | 2059.58 |
| SV220 | CoNH$_3^+$ | 10 Co-NH$_3^+$ | C$_{86}$H$_{188}$O$_{24}$N$_{10}$P$_6$ | 1932.35 |

Figure 5

*Acyclic Primary Amines*

| | | | | |
|---|---|---|---|---|
| SV112 | 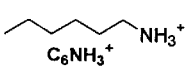 C₆NH₃⁺ | 7 $C_6NH_3^+$ | $C_{48}H_{123}O_{24}N_7P_6$ | 1368.39 |
| SV115 | | 9 $C_6NH_3^+$ | $C_{60}H_{153}O_{24}N_9P_6$ | 1570.78 |
| SV135 | 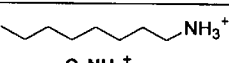 C₈NH₃⁺ | 9 $C_8NH_3^+$ | $C_{78}H_{189}O_{24}N_9P_6$ | 1821 |

*Amino-acids*

| | | | | |
|---|---|---|---|---|
| SV47 | 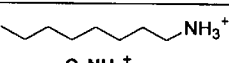 Me-PheAla-NH₃⁺ | 5 Me-PheAla-NH₃⁺ | $C_{56}H_{76}O_{34}N_5P_6$ | 1549.08 |
| SV48 | | 9 Me-PheAla-NH₃⁺ | $C_{96}H_{132}O_{42}N_9P_6$ | 2270.00 |
| SV55 | 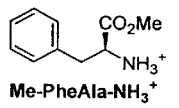 Et-PheAla-NH₃⁺ | 7 Et-PheAla-NH₃⁺ | $C_{83}H_{123}O_{38}N_7P_6$ | 2012.77 $H_{6.16}N_{4.87}C_{49..53}$ |
| SV56 | | 6 Et-PheAla-NH₃⁺ | $C_{72}H_{108}O_{36}N_6P_6$ | 1819.52 $H_{5.98}C_{47.53}N_{4.62}$ |
| SV57 | 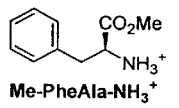 tBu-iLeu-NH₃⁺ | 8 tBu-iLeu-NH₃⁺ | $C_{78}H_{154}O_{40}N_8P_6$ | 1819.52 $H_{5.98}C_{47.53}N_{4.62}$ |
| SV68 | 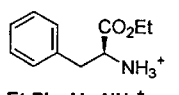 Et-Tyr-NH₃⁺ | 10 Et-Tyr-NH₃⁺ | $C_{116}H_{168}O_{54}N_{10}P_6$ | 2752.51 $H_{6.15}C_{50.62}N_{5.09}$ |
| SV80 | 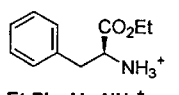 Et-Try-NH₃⁺ | 7 Et-Try-NH₃⁺ | $C_{97}H_{130}O_{38}N_{14}P_6$ | 2286.03 |

Figure 6

Secondary Amines

| Reference | Counter-cation | Number | Mol. Formula | Mol. Weight (g.mol$^{-1}$) |
|---|---|---|---|---|
| IC2P$_1$ | 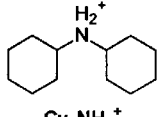 Cy$_2$NH$_2^+$ | 2 Cy$_2$NH$_3^+$ 10 Na$^+$ | C$_{30}$H$_{54}$O$_{24}$N$_2$P$_6$Na$_{10}$ | 1242.50 |
| IC2P$_2$ | | 8 Cy$_2$NH$_3^+$ | C$_{102}$H$_{202}$O$_{24}$N$_8$P$_6$ | 2110.63 |
| SV46 | PiNH$_2^+$ 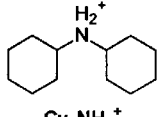 | 9 PiNH$_2^+$ | C$_{51}$H$_{117}$O$_{24}$N$_9$P$_6$ | 1426.39 |
| SV53 | 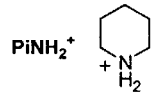 DHQ-NH$_2^+$ | 9 PiNH$_2^+$ | C$_{87}$H$_{171}$O$_{24}$N$_9$P$_6$ | 1913.22 H$_{9.01}$ C$_{54.62}$ N$_{6.59}$ |
| SV58 | 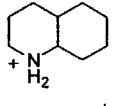 iPr$_2$-NH$_2^+$ | 12 iPr$_2$NH$_2^+$ | C$_{78}$H$_{198}$O$_{24}$N$_{12}$P$_6$ | 1874.36 H$_{10.65}$ C$_{49.98}$ N$_{8.97}$ |
| SV59 | 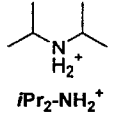 tBu-Pro-NH$_2^+$ | 8 tBu-ProNH$_2^+$ | C$_{78}$H$_{154}$O$_{40}$N$_8$P$_6$ | 1874.36 H$_{7.65}$ C$_{46.15}$ N$_{5.52}$ |

Figure 7
*Tertiary Amines*
| Reference | Counter-cation | Number | Mol. Formula | Mol. Weight (g.mol$^{-1}$) |
|---|---|---|---|---|
| IP$_{12}$ | 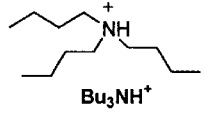 Bu$_3$NH$^+$ | 7 Bu$_3$NH$^+$ 5 Na$^+$ | C$_{90}$H$_{202}$O$_{24}$N$_7$P$_6$Na$_6$ | 2067.43 |
| SV42 | 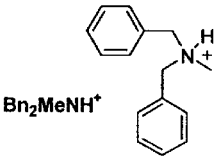 Bn$_2$MeNH$^+$ | 6 Bn$_2$MeNH$^+$ | C$_{96}$H$_{120}$O$_{24}$N$_6$P$_6$ | 1550.66<br>H$_{6.27}$ C$_{59.81}$ N$_{4.36}$ |
| SV44 | 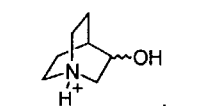 QLNH$^+$ | 7 QLNH$^+$ | C$_{55}$H$_{109}$O$_{31}$N$_7$P$_6$ | 1550.35 |
| SV45 | 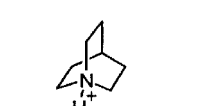 QNH$^+$ | 12 QNH$^+$ | C$_{90}$H$_{174}$O$_{24}$N$_{12}$P$_6$ | 1994.30<br>H$_{8.79}$ C$_{54.2}$ N$_{8.43}$ |
| SV99 | 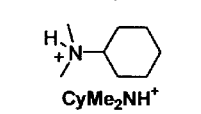 CyMe$_2$NH$^+$ | 6 CyMe$_2$NH$^+$ | C$_{54}$H$_{114}$O$_{24}$N$_6$P$_6$ | 1417.38<br>H$_{8.11}$ C$_{45.76}$ N$_{5.93}$ |

Figure 8
Diamines
| Reference | Counter-cation | Number | Mol. Formula | Mol. Weight (g.mol⁻¹) |
|---|---|---|---|---|
| SV72 | 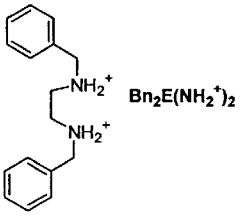 Bn₂E(NH₂⁺)₂ | 5 Bn₂E(NH⁺)₂ | $C_{86}H_{108}O_{24}N_{10}P_6$ | 1851.71 $H_{5.88}C_{55.78}N_{7.56}$ |
| SV76 | | 4 Bn₂E(NH⁺)₂ | $C_{70}H_{88}O_{24}N_8P_6$ | 1611.36 $H_{5.5}C_{52.18}N_{6.95}$ |
| SV73 | 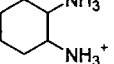 Cy(NH₃⁺)₂ | 4 Cy(NH₃⁺)₂ | $C_{30}H_{68}O_{24}N_8P_6$ | 1110.76 |
| SV92 | | 5 Cy(NH₃⁺)₂ | $C_{36}H_{88}O_{24}N_{10}P_6$ | 1231.00 |
| SV89 | 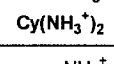 Men-(NH₃⁺)₂ | 8 Men-(NH₃⁺)₂ | $C_{86}H_{228}O_{24}N_{16}P_6$ | 2056.71 |
| SV94 | 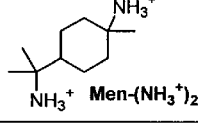 Cy(CH₂NH₃⁺)₂ | 5 Cy-(CH₂NH₃⁺)₂ | $C_{46}H_{108}O_{24}N_{10}P_6$ | 1371.27 |
| SV95 | 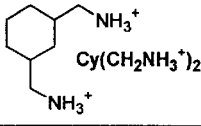 Ph₂E(NH₃⁺)₂ | 5 Ph₂E(NH₃⁺)₂ | $C_{76}H_{98}O_{24}N_{10}P_6$ | 1721.52 |
| SV97 |  Cy₁Pip | 9 Cy₁Pip | $C_{96}H_{192}O_{24}N_{10}P_6$ | 2056.50 |

Figure 9

*Triamines*

| Reference | Counter-cation | Number | Mol. Formula | Mol. Weight (g.mol$^{-1}$) |
|---|---|---|---|---|
| SV101 | Cy$_2$DAP (SV91) | 2 Cy$_2$DAP | C$_{42}$H$_{92}$O$_{24}$N$_6$P$_6$ | 1251.07 |
| SV120 | | 3.6 Cy$_2$DAP | C$_{71}$H$_{145}$O$_{24}$N$_{11}$P$_6$ | 1722.85 |

*Tetra-amines*

| Ref | Counter-cation | Number | Mol. Formula | Mol. Weight (g.mol$^{-1}$) |
|---|---|---|---|---|
| SV102 | Cy$_3$TREN (SV98) | 3 Cy$_3$TREN | C$_{78}$H$_{162}$O$_{24}$N$_{12}$P$_6$ | 1838.07 |
| SV106 | Cy$_2$BAP (SV103) | 4 Cy$_2$BAP | C$_{94}$H$_{194}$O$_{24}$N$_{16}$P$_6$ | 2118.53 |
| SV137 | Ch$_3$TREN (SV127) | 2 Ch$_3$TREN | C$_{60}$H$_{120}$O$_{24}$N$_8$P$_6$ | 1523.51 |
| SV141 | Co$_2$BAP (SV129) | 3 Co$_2$BAP | C$_{84}$H$_{174}$O$_{24}$N$_{12}$P$_6$ | 1922.2 |
| SV202 | Cyclam-(C$_6$)$_4$ (SV198) | 2 Cyclam-(C$_6$)$_4$ | C$_{74}$H$_{162}$O$_{24}$N$_8$P$_6$ | 1733.99 |

Figure 10

*Hexa-amines*

| Ref | Counter-cation | Number | Mol. Formula | Mol. Weight (g.mol$^{-1}$) |
|---|---|---|---|---|
| SV216 | | 1 Neomycin/IHP | $C_{29}H_{64}O_{37}N_6P_6$ | 1274.69 |
| SV217 | Neomycine | 2 Neomycin/IHP | $C_{52}H_{110}O_{50}N_{12}P_6$ | 1889.35 |

Figure 11  Partition coefficients of IHP ammonium salts (at 30 mM).

Primary amines

$K_{ow}$ = octanol/water partition coefficient
$K_{os}$ = octanol/serum partition coefficient

*aliphatic amines*   refers to the number of ammoniums associated to IHP

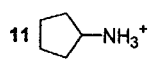
11, $K_{ow} < 10^{-3}$

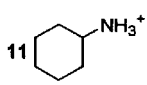
11, $K_{ow} = 14.10^{-3}$, $K_{os} < 10^{-3}$

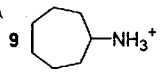
9, $K_{ow} = 0.84$, $K_{os} = 0.18$

7, $K_{ow} < 10^{-3}$

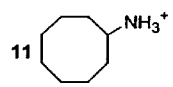
11, $K_{ow} = 8.98$ (18mM), $K_{os} = 1.85$ (18mM)

7, $K_{ow} < 10^{-3}$

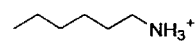
$K_{ow} = 2.04$, $K_{os} = 4.5$

*amino esters*

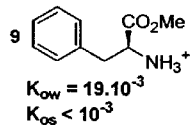
9, $K_{ow} = 19.10^{-3}$, $K_{os} < 10^{-3}$

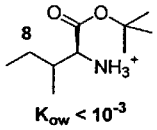
8, $K_{ow} < 10^{-3}$

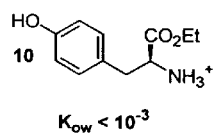
10, $K_{ow} < 10^{-3}$

Secondary amines

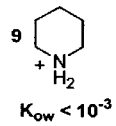
9, $K_{ow} < 10^{-3}$

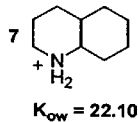
7, $K_{ow} = 22.10^{-3}$, $K_{os} < 10^{-3}$

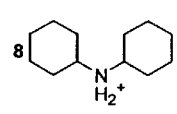
8, $K_{ow} = 0.74$, $K_{os} = 17.10^{-3}$

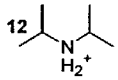
12, $K_{ow} < 10^{-3}$

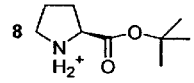
8, $K_{ow} < 10^{-3}$

Tertiary amines

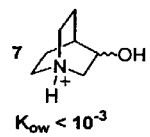
7, $K_{ow} < 10^{-3}$

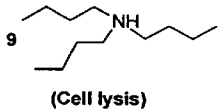
9, (Cell lysis)

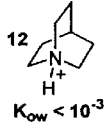
12, $K_{ow} < 10^{-3}$

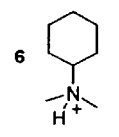
6, $K_{ow} < 10^{-3}$

Water solubility < 1mM

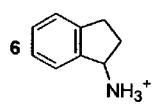
6

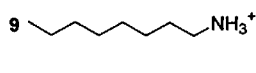
9

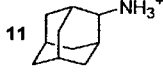
11

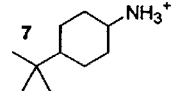
7

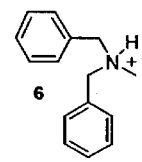
6

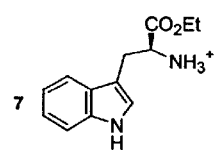
7

Experiments SV136 and SV142.

Compound SV131 (IHP, 11 cyclooctylammonium) was dissolved in 1-octanol at various concentrations and agitated with an equal volume of artificial serum (SV136) or human serum (SV142).

Experiment SV134.

Compound SV75 (IHP, 9 cycloheptylammonium) was dissolved in octanol at various concentrations and agitated with an equal volume of water.

*IHP uptake in 1-octanol by cyclooctylammonium ions.* IHP, dodecasodium form, was dissolved in human serum ([IHP] = 22 mM, pH = 7.4). Each samples were agitated 2 days with an equal volume of octanolic solution of cyclooctylamine,HCl at different concentrations. Partition coefficients $K_{OS}$ were measured by $^{31}$P-NMR.

Figure 14    $P_{50}$ values obtained from $O_2$-dissociation curves using whole blood.

Figure 15

| Effector | P50 CONTROL WB mmHg | P50 EFF: WB mmHg | CONC. EFF mM | CONC EFF:WB mM | OSMOL. EFF mOsM | pH EFF. | pH EFF:WB or EFF:fHb | Volume Ratio EFF:WB |
|---|---|---|---|---|---|---|---|---|
| HBS+ | | | | | 310 | | 7.22 | |
| fHb in HBS+ | | | | | | | 7.22 | |
| ICP6 | | | | | | | | |
| WB | 27.5 | 39 | 30 | 22 | 220 | | 7.23 | 1:0.375 |
| WB | 27.5 | 27.5 | 30 | 22 | 312 | | 7.2 | 1:0.375 |
| WB | 27.5 | 31 | 30 | 22 | 262 | | 7.21 | 1:0.375 |
| WB | 27.5 | 27.5 | 60 | 44 | 318 | | 7.32 | 1:1.5 |
| fHb | 16 | 43.5 | | | | | 7.18 | 0.25 µM EFF |
| IC2P1 | | | | | | | | |
| WB | 38.5 | 39.5 | 30 | 22 | 160 | | 6.04 | 1:0.375 |
| WB | 38.5 | 39.5 | 30 | 22 | 160 | | 6.03 | 1:0.375 | fHb = free hemoglobin; WB = whole blood; EFF = effector.

Figure 16

| Effector | P50 CONTROL WB mmHg | P50 EFF: WB mmHg | CONC. EFF mM | CONC EFF:WB mM | OSMOL. EFF mOsM | pH EFF. | pH EFF:WB or EFF:*f*Hb | Volume Ratio EFF:WB |
|---|---|---|---|---|---|---|---|---|
| IC2P2 | | | | | | | | |
| WB | 38 | 41 | 30 | 22 | 302 | 7.44 | 6.94 | 1:0.375 |
| WB | 38 | 39.5 | 30 | 22 | 323 | | 7.21 | 1:0.375 |
| *f*Hb | 16.5 | 41.5 | | | | | 7.17 | 0.25 µM EFF |
| SV44 | | | | | | | | |
| WB | 37.5 | 40 | 30 | 22 | 158 | | 7.23 | 1:0.375 |
| WB | 37.5 | 37.5 | 30 | 12 | 315 | | 6.98 | 1:1.5 |
| *f*Hb | 16 | 42.5 | | | | | 7.17 | 0.25 µM EFF |
| SV46 | | | | | | | | |
| WB | 38.5 | 36 | 30 | 12 | 319 | | 7.13 | 1:1.5 |
| *f*Hb | 16 | 42 | | | | | | 0.25 µM EFF |
| SV47 | | | | | | | | |
| WB | 38.5 | 38.5 | 30 | 22 | 173 | | 6.93 | 1:0.375 |
| WB | 38.5 | 38.5 | 30 | 12 | 338 | | 7.41 | 1:1.5 |
| *f*Hb | 16 | 45.5 | | | | | 7.11 | 0.25 µM EFF |
| SV48 | | | | | | | | |
| WB | 38.5 | 36 | 30 | 22 | 187 | | 6.88 | 1:0.375 |
| WB | 38.5 | 37 | 30 | 12 | 326 | | 7.26 | 1:1.5 |
| *f*Hb | 16 | 48 | | | | | 7.1 | 0.25 µM EFF |
| SV51 | | | | | | | | |
| WB | 25 | 28.5 | 30 | 22 | 220 | 7.67 | 7.36 | 1:0.375 |
| WB | 25 | 24.5 | 30 | 12 | 220 | 7.67 | | 1:1.5 |
| WB | 24.5 | 27 | 30 | 12 | 220 | 7.51 | 6.99 | 1:1.5 |
| WB | 28.5 | 28.5 | 30 | 12 | 344 | 7.64 | 7.27 | 1:1.5 |
| *f*Hb | 16 | 44 | | | | | 7.19 | 0.25 µM EFF |
| SV52 | | | | | | | | |
| WB | 38.5 | 38.5 | 30 | 22 | 200 | | 6.4 | 1:0.375 |
| *f*Hb | 16 | 45.5 | | | | | 7.15 | 0.25 µM EFF |
| SV53 | | | | | | | | |
| WB | 24.5 | 27 | 30 | 12 | 221 | 7.12 | 6.6 | 1:1.5 |
| WB | 28.5 | 28.5 | 30 | 12 | 362 | 7.86 | 7.27 | 1:1.5 |
| *f*Hb | 16 | 43 | | | | | 7.18 | 0.25 µM EFF |

*f*Hb = free hemoglobin; WB = whole blood; EFF = effector.

Figure 17

| Effector | | P50 CONTROL WB mmHg | P50 EFF: WB mmHg | CONC. EFF mM | CONC EFF:WB mM | OSMOL. EFF mOsM | pH EFF. | pH EFF:WB or EFF:fHb | Volume Ratio EFF:WB |
|---|---|---|---|---|---|---|---|---|---|
| SV55 | | | | | | | | | |
| | WB | 28.5 | 28.5 | 30 | 12 | 346 | 7.58 | 7.21 | 1:1.5 |
| | fHb | 16 | 48.5 | | | | | 7.15 | 0.25 µM EFF |
| SV56 | | | | | | | | | |
| | WB | 28.5 | 28.5 | 30 | 12 | 325 | 7.35 | 7.36 | 1:1.5 |
| | fHb | 16 | 41 | | | | | 7.15 | 0.25 µM EFF |
| SV45 | | | | | | | | | |
| | WB | 32.5 | 34.5 | 30 | 22 | 240 | 7.38 | | 1:0.375 |
| | fHb | 16.5 | 45.5 | | | | | 7.18 | 0.25 µM EFF |
| SV57 | | | | | | | | | |
| | WB | 32.5 | Lysis | 30 | 22 | 323 | 7.28 | | 1:0.375 |
| | fHb | 16.5 | 43 | | | | | 7.16 | 0.25 µM EFF |
| SV58 | | | | | | | | | |
| | WB | 32.5 | 35.6 | 30 | 22 | 184 | 7.41 | | 1:0.375 |
| | fHb | 16.5 | 43 | | | | | 7.17 | 0.25 µM EFF |
| SV59 | | | | | | | | | |
| | WB | 32.5 | 35.3 | 30 | 22 | 129 | 7.32 | | 1:0.375 |
| | fHb | 16.5 | 41.5 | | | | | 7.16 | 0.25 µM EFF |
| SV68 | | | | | | | | | |
| | WB | 38 | 36 | 30 | 12 | 341 | | 7.38 | 1:1.5 |
| | fHb | 16.5 | 50 | | | | | 7.15 | 0.25 µM EFF |
| SV73 | | | | | | | | | |
| | WB | 38 | 36 | 30 | 12 | 72 | | 6.17 | 1:1.5 |
| | WB | 38 | 36 | 30 | 12 | 335 | | 7.31 | 1:1.5 |
| | WB | 38 | 57 | 30 | 22 | 68 | | 7.54 | 1:0.375 |
| | fHb | 16.5 | 43 | | | | | 7.2 | 0.25 µM EFF |
| SV75 | | | | | | | | | |
| | fHb | 16.5 | 45 | | | | | 7.2 | 0.25 µM EFF |
| SV78 | | | | | | | | | |
| | WB | 38 | 36 | 30 | 12 | 309 | | 7.3 | 1:1.5 |
| | fHb | 16.5 | 46 | | | | | 7.2 | 0.25 µM EFF |
| SV81 | | | | | | | | | |
| | WB | 38 | 36 | 30 | 12 | 341 | | 7.38 | 1:1.5 |
| | fHb | 16.5 | 44 | | | | | 7.2 | 0.25 µM EFF | fHb = free hemoglobin; WB = whole blood; EFF = effector.

Figure 19
$K_{ow}$ = octanol/water partition coefficient
$K_{os}$ = octanol/serum partition coefficient
Polyamines
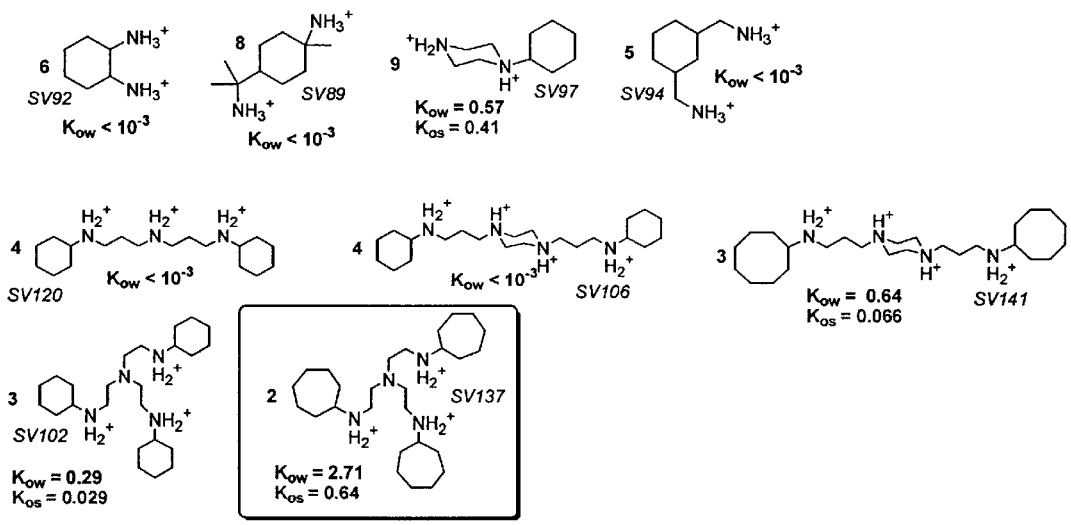
Water solubility < 1mM
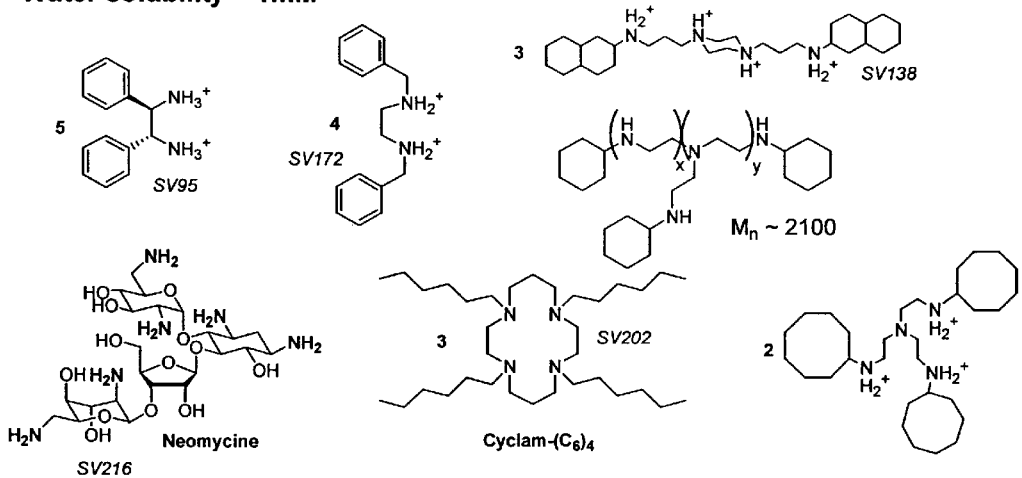

AMMONIUM SALTS OF INOSITOL HEXAPHOSPHATE, AND USES THEREOF

RELATED APPLICATION INFORMATION

This application claims the benefit of priority under 35 U.S.C. section 119(e) to Provisional Patent Applications Nos. 60/222,089, filed Aug. 1, 2000. This application is hereby incorporated by reference in its entirety.

BACKGROUND OF THE INVENTION

I. Ischemia

Ischemic insult, i.e., the localized deficiency of oxygen to an organ or skeletal tissue, is a common and important problem in many clinical conditions. The problem is especially acute in organ transplant operations in which a harvested organ is removed from a body, isolated from a blood source, and thereby deprived of oxygen and nutrients for an extended period of time. Ischemic insult also occurs in certain clinical conditions, such as sickle cell anemia and septic shock, which may result from hypotension or organ dysfunction. Depending on the duration of the insult, the ischemia can disturb cellular metabolism and ion gradients, and ultimately cause irreversible cellular injury and death.

Arguably, heart attacks and stroke are the most widely recognized example of the damage resulting from ischemia. Myocardial ischemia is a condition wherein there is insufficient blood supply to the myocardium (the muscles of the heart) to meet its demand for oxygen. The ultimate result of persistent myocardial ischemia is necrosis or death of a portion of cardiac muscle tissue, known as a myocardial infarct, commonly known as a heart attack.

Insufficient blood supply to the myocardium is generally due to an obstruction or thrombus in an artery supplying blood to the myocardium. Another cause can be atrial fibrillation, wherein the increased heart rate associated with atrial fibrillation increases the work, and hence the blood demand of the myocardium, while the atrial fibrillation at the same time reduces the blood supply.

Whereas stroke is defined as a sudden impairment of body functions caused by a disruption in the supply of blood to the brain. For instance, a stroke occurs when blood supply to the brain is interrupted for any reason, including hemorrhage, low blood pressure, clogging by atherosclerotic plaque, a blood clot, or any particle. Because of the blockage or rupture, part of the brain fails to get the supply of blood and oxygen that it requires. Brain tissue that receives an inadequate supply of blood is said to be ischemic. Deprived of oxygen and nutrients, nerve cells and other cell types within the brain begin to fail, creating an infarct (an area of cell death, or necrosis). As the neurons fail and die, the part of the body controlled by those neurons can no longer function. The devastating effects of ischemia are often permanent because brain tissue has very limited repair capabilities and lost neurons are typically not regenerated.

Cerebral ischemia may be incomplete (blood flow is reduced but not entirely cut off), complete (total loss of tissue perfusion), transient or permanent. If ischemia is incomplete and persists for no more than ten to fifteen minutes, neural death may not occur. More prolonged or complete ischemia results in infarction. Depending on the site and extent of the infarction, mild to severe neurological disability or death will follow.

To a modest extent, the brain is protected against cerebral ischemia by compensatory mechanisms, including collateral circulation (overlapping local blood supplies), and arteriolar auto-regulation (local smooth muscle control of blood flow in the smallest arterial channels). If compensatory mechanisms operate efficiently, slightly diminished cerebral blood flow produces neither tissue ischemia nor abnormal signs and symptoms. Usually, such mechanisms must act within minutes to restore blood flow if permanent infarction damage is to be avoided or reduced. Arteriolar auto-regulation works by shunting blood from noncritical regions to infarct zones.

Even in the face of systemic hypotension, auto-regulation may be sufficient to adjust the circulation and thereby preserve the vitality and function of brain or heart tissue. Alternatively, ischemia may be sufficiently prolonged and compensatory mechanisms sufficiently inadequate that a catastrophic stroke or heart attack results.

Ischemia is also associated with various clinical conditions, such as septic shock. Septic shock as a result of hypotension and organ dysfunction in response to infectious sepsis is a major cause of death. The manifestations of sepsis include those related to the systemic response to infection (tachycardia, tachypnea alterations in temperature and leukocytosis) and those related to organ-system dysfunction (cardiovascular, respiratory, renal, hepatic and hematologic abnormalities). Furthermore, the lipopolysaccharide (LPS) of gram-negative bacteria is considered to be the most important exogenous mediator of acute inflammatory response to septic shock. The LPS or endotoxin released from the outer membrane of gram-negative bacteria results in the release of cytokines and other cellular mediators, including tumor necrosis factor alpha (TNF alpha), interleukin-1 (Il-1), interleukin-6 (Il-6) and thromboxane A2. Extreme levels of these mediators are known to trigger many pathological events, including fever, shock, and intravascular coagulation, leading to ischemia and organ failure.

II. Hemoglobin

Hemoglobin is a tetrameric protein which delivers oxygen via an allosteric mechanism. Oxygen binds to the four hemes of the hemoglobin molecule. Each heme contains porphyrin and iron in the ferrous state. The ferrous iron-oxygen bond is readily reversible. Binding of the first oxygen to a heme releases much greater energy than binding of the second oxygen molecule, binding of the third oxygen releases even less energy, and binding of the fourth oxygen releases the least energy.

In blood, hemoglobin is in equilibrium between two allosteric structures. In the "T" (for tense) state, hemoglobin is deoxygenated. In the "R" (for relaxed) state, hemoglobin is oxygenated. An oxygen equilibrium curve can be scanned to observe the affinity and degree of cooperativity (allosteric action) of hemoglobin. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined (i.e., this is the pressure in mm Hg when the scanned hemoglobin sample is 50% saturated with oxygen). Under physiological conditions (i.e., 37 C, pH=7.4, and partial carbon dioxide pressure of 40 mm Hg), the $P_{50}$ value for normal adult hemoglobin (HbA) is around 26.5 mm Hg. If a lower than normal $P_{50}$ value is obtained for the hemoglobin being tested, the scanned curve is considered to be "left-shifted" and the presence of high oxygen-affinity hemoglobin is indicated. Conversely, if a higher than normal $P_{50}$ value is obtained for the hemoglobin being tested, the scanned curve is considered to be "right-shifted", indicating the presence of low oxygen-affinity hemoglobin.

It has been proposed that influencing the allosteric equilibrium of hemoglobin is a viable avenue of attack for treating diseases. The conversion of hemoglobin to a high affinity state is generally regarded to be beneficial in resolving problems with (deoxy)hemoglobin-S (i.e., sickle cell anemia). The conversion of hemoglobin to a low affinity state is believed to have general utility in a variety of disease states where tissues suffer from low oxygen tension, such as ischemia and radio sensitization of tumors. Several synthetic compounds have been identified which have utility in the allosteric regulation of hemoglobin and other proteins. For example, several new compounds and methods for treating sickle cell anemia which involve the allosteric regulation of hemoglobin are reported in U.S. Pat. No. 4,699,926 to Abraham et al., U.S. Pat. No. 4,731,381 to Abraham et al., U.S. Pat. No. 4,731,473 to Abraham et al., U.S. Pat. No. 4,751,244 to Abraham et al., and U.S. Pat. No. 4,887,995 to Abraham et al. Furthermore, in both Perutz, "Mechanisms of Cooperativity and allosteric Regulation in Proteins", *Quarterly Reviews of Biophysics* 22, 2 (1989), pp. 163–164, and Lalezari et al., "LR16, a compound with potent effects on the oxygen affinity of hemoglobin, on blood cholesterol, and on low density lipoprotein", *Proc. Natl. Acad. Sci, USA* 85 (1988), pp. 6117–6121, compounds which are effective allosteric hemoglobin modifiers are discussed. In addition, Perutz et al. has shown that a known antihyperlipoproteinemia drug, bezafibrate, is capable of lowering the affinity of hemoglobin for oxygen (See "Bezafibrate lowers oxygen affinity of hemoglobin", *Lancet* 1983, 881).

Human normal adult hemoglobin ("HbA") is a tetrameric protein containing two alpha chains having 141 amino acid residues each and two beta chains having 146 amino acid residues each, and also bearing prosthetic groups known as hemes. The erythrocytes help maintain hemoglobin in its reduced, functional form. The heme-iron atom is susceptible to oxidation, but may be reduced again by one of two systems within the erythrocyte, the cytochrome b5, and glutathione reduction systems.

Hemoglobin is able to alter its oxygen affinity, thereby increasing the efficiency of oxygen transport in the body due to its dependence on 2,3-DPG, an allosteric regulator. 2,3-DPG is present within erythrocytes at a concentration that facilitates hemoglobin to release bound oxygen to tissues. Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two alpha- and two beta-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

It is known that hemoglobin specifically binds small polyanionic molecules, especially 2,3-diphosphoglycerate (DPG) and adenosine triphosphate (ATP), present in the mammalian red cell (Benesch and Benesch, *Nature*, 221, p. 618, 1969). This binding site is located at the centre of the tetrameric structure of hemoglobin (Arnone, A., *Nature*, 237, p. 146, 1972). The binding of these polyanionic molecules is important in regulating the oxygen-binding affinity of hemoglobin since it allosterically affects the conformation of hemoglobin leading to a decrease in oxygen affinity (Benesch and Benesch, *Biochem. Biophys. Res. Comm.*, 26, p. 162, 1967). Conversely, the binding of oxygen allosterically reduces the affinity of hemoglobin for the polyanion. (Oxy) hemoglobin therefore binds DPG and ATP weakly. This is shown, for example, by studies of spin-labeled ATP binding to oxy- and deoxyhemoglobin as described by Ogata and McConnell (*Ann. N.Y. Acad. Sc.*, 222, p. 56, 1973). In order to exploit the polyanion-binding specificity of hemoglobin, or indeed to perform any adjustment of its oxygen-binding affinity by chemically modifying the polyanion binding site, it has been necessary in the prior art that hemoglobin be deoxygenated. However, hemoglobin as it exists in solutions, or mixtures exposed to air, is in its oxy state, i.e., (oxy)hemoglobin. In fact it is difficult to maintain hemoglobin solutions in the deoxy state, (deoxy) hemoglobin, throughout a chromatographic procedure. Because of these difficulties, the technique of affinity chromatography has not been used in the prior art to purify hemoglobin.

Hemoglobin has also been administered as a pretreatment to patients receiving chemotherapeutic agents or radiation for the treatment of tumors (U.S. Pat. No. 5,428,007; WO 92/20368; WO 92/20369), for prophylaxis or treatment of systemic hypotension or septic shock induced by internal nitric oxide production (U.S. Pat. No. 5,296,466), during the perioperative period or during surgery in a method for maintaining a steady-state hemoglobin concentration in a patient (WO 95/03068), and as part of a perioperative hemodilution procedure used prior to surgery in an autologous blood use method (U.S. Pat. Nos. 5,344,393 and 5,451,205). When a patient suffers a trauma (i.e., a wound or injury) resulting, for example, from surgery, an invasive medical procedure, or an accident, the trauma disturbs the patient's homeostasis. The patient's body biologically reacts to the trauma to restore homeostasis. This reaction is referred to herein as a naturally occurring stress response. If the body's stress response is inadequate or if it occurs well after the trauma is suffered, the patient is more prone to develop disorders.

III. Reduction of the Oxygen-Affinity of Hemoglobin

The major function of erythrocytes consists in the transport of molecular oxygen from the lungs to the peripheral tissues. The erythrocytes contain a high concentration of hemoglobin (30 pg per cell=35.5 g/100 ml cells) which forms a reversible adduct with $O_2$. The $O_2$-partial pressure in the lung is about. 100 mm Hg, in the capillary system is about. 70 mm Hg, against which $O_2$ must be dissociated from the oxygenated hemoglobin. Under physiological conditions, only about 25% of the oxygenated hemoglobin may be deoxygenated; about. 75% is carried back to the lungs with the venous blood. Thus, the major fraction of the hemoglobin-$O_2$ adduct is not used for the $O_2$ transport.

Interactions of hemoglobin with allosteric effectors enable an adaptation to the physiological requirement of maximum $O_2$ release from the hemoglobin-$O_2$ adduct with simultaneous conservation of the highest possible $O_2$ partial pressure in the capillary system. 2,3-Diphosphoglycerate increases the half-saturation pressure of stripped hemoglobin at pH 7.4 from $P(O_2)$ (½)=9.3 mm Hg (37 C.), and 4.3 mm Hg (25 C.) to $P(O_2)$ (½)=23.7 mm Hg (37 C.), and 12.0 mm Hg (25 C.), respectively (Imai, K. and Yonetani, T.

(1975), *J. Biol. Chem.* 250, 1093–1098). A significantly stronger decrease of the $O_2$ affinity, i.e., enhancement of the $O_2$ half-saturation pressure has been achieved for stripped hemoglobin by binding of inositol hexaphosphate (phytic acid; IHP) (Ruckpaul, K. et al. (1971) *Biochim. Biophys. Acta* 236, 211–221) isolated from vegetal tissues. Binding of IHP to hemoglobin increases the $O_2$ half-saturation pressure to $P(O_2)$ (½)=96.4 mm Hg (37 C.), and $P(O_2)$ (½)=48.4 mm Hg (25 C.), respectively. IHP, like 2,3-diphosphoglycerate and other polyphosphates cannot penetrate the erythrocyte membrane.

Furthermore, the depletion of DPG and ATP in stored red cells leads to a progressive increase of the oxygen affinity of hemoglobin contained therein (Balcerzak, S. et al. (1972) *Adv. Exp. Med. Biol.* 28, 453–447). The $O_2$-binding isotherms are measured in the absence of $CO_2$ and at constant pH (pH 7.4) in order to preclude influences of these allosteric effectors on the half-saturation pressure. The end point of the progressive polyphosphate depletion is defined by $P(O_2)$ (½)=4.2 mm Hg, which is the half-saturation pressure of totally phosphate-free (stripped) hemoglobin; the starting point, i.e., $P(O_2)$ (½) of fresh erythrocytes, depends on the composition of the suspending medium. From these polyphosphate depletion curves a new functional parameter of stored erythrocytes can be determined, the so-called half-life time of intra-erythrocytic polyphosphate: 9 d (days) in isotonic 0.1 M bis-Tris buffer pH 7.4: and 12 d (days) in acid-citrate-dextrose conservation (ACD) solution.

Several years ago, it was discovered that the antilipidemic drug clofibric acid lowered the oxygen affinity of hemoglobin solutions (Abraham et al., *J. Med. Chem.* 25, 1015 (1982), and Abraham et al., *Proc. Natl. Acad. Sci USA* 80, 324 (1983)). Bezafibrate, another antilipidemic drug, was later found to be much more effective in lowering the oxygen affinity of hemoglobin solutions and suspensions of fresh, intact red cells (Perutz et al., *Lancet,* 881, Oct. 15, 1983). Subsequently, X-ray crystallographic studies have demonstrated that clofibric acid and bezafibrate bind to the same sites in the central water cavity of deoxyhemoglobin, and that one bezafibrate molecule will span the sites occupied by two clofibric acid molecules. Bezafibrate and clofibric acid act by stabilizing the deoxy structure of hemoglobin, shifting the allosteric equilibrium toward the low affinity deoxy form. Bezafibrate and clofibric acid do not bind in any specific manner to either oxy- or carbon-monoxyhemoglobin.

In more recent investigations, a series of urea derivatives [2-[4-[[(arylamino)carbonyl]amino]phenoxy]-2-methylpropionic acids] was discovered that has greater allosteric potency than bezafibrate at stabilizing the deoxy structure of hemoglobin and shifting the allosteric equilibrium toward the low oxygen affinity form (Lalezari, *Proc. Natl. Acad. Sci. USA* 85, 6117 (1988)).

Drugs which can allosterically modify hemoglobin toward a lower oxygen affinity state hold potential for many clinical applications, such as for the treatment of ischemia, shock, and polycythemia, and as radiosensitizing agents. Unfortunately, the effects of bezafibrate and the urea derivatives discussed above have been found to be significantly inhibited by serum albumin, the major protein in blood serum (Lalezari et al., *Biochemistry,* 29, 1515 (1990)). Therefore, the clinical usefulness of these drugs is seriously undermined because in whole blood and in the body, the drugs would be bound by serum albumin instead of reaching the red cells, crossing the red cell membrane, and interacting with hemoglobin protein molecule to produce the desired effect.

There has been considerable interest in medicine, the military health services, and the pharmaceutical industry in finding methods to increase blood storage life; to discover radio sensitization agents; and to develop new blood substitutes. In all these instances, the availability of either autologous blood or recombinant Hb solutions is of major interest, provided the oxygen affinity can be decreased to enhance oxygen delivery to the tissues.

2,3-Diphosphoglycerate (2,3-DPG) is the normal physiological ligand for the allosteric site on hemoglobin. However, phosphorylated inositols are found in the erythrocytes of birds and reptiles. Specifically, inositol hexaphosphate (IHP), as known as phytic acid, displaces hemoglobin-bound 2,3-DPG, binding to the allosteric site with one-thousand times greater affinity. Unfortunately, IHP is unable to pass unassisted across the erythrocyte membrane.

As emphasized in phase transfer catalysis, it has long been recognized that organic and inorganic anions can be efficiently solubilized in organic media when associated to tri- or tetra-alkyl ammoniums counter-cations. IHP is a highly charged polyphosphate insoluble in many organic solvents, but is also capable of multiple ionic bonds with organic ammoniums. Since pKa values of all acidic protons of IHP have been measured either by NMR (L. R. Isbrandt, R. P. Oertel *J. Am. Chem. Soc.* 1980, 102, 3144–48), or by potentiometric methods (H. Bieth, B. Spiess J. Chem. Soc., Faraday Transaction 1 1986, 25, 6701–6705), it has been established that IHP bears 7 or 8 charges at physiological pH. It also means that IHP can be associated to at least seven lipophilic cations in physiological conditions. Thus, as a function of the associated ammoniums, the lipophilicity can theoretically be shifted to a cell-membrane compatible IHP-complex, the ideal case being a poly-ammonium IHP derivative that would be soluble in both water and low polarity media. Because of the emergence of the gene transfection research field a huge number of cationic lipids are described in the literature, and extensively reviewed. In most of the cases these chemical vectors are lipids functionnalized with amines, poly-amines, (poly-) guanidiniums, and, in rare cases, phosphoniums. These cationic lipids are designed for gene delivery, and the mechanism by which they transport oligonucleotides across biological membranes may be very different for the delivery of a small poly-anionic molecule such as phytic acid.

Moreover, to avoid the technical problems associated to drug delivery mediated by liposomes or vesicles, we decided, as a first approach, to prepare water-soluble lipophilyzed IHP derivatives. Thus, a first library of IHP-ammoniums salts has been prepared from commercially available non-lipidic amines in order to assess the structural parameters allowing both the transport (by increasing the lipophilicity) and the water solubilities of the salts (for the improvement of the bioavailability). Both the biological and physical properties of each salts have been evaluated by the measurement of $O_2$ dissociation curves, performed on whole blood, and 1-octanol/water partition coefficients, respectively.

IV Enhanced Oxygen Delivery in Mammals

The therapy of oxygen deficiencies requires the knowledge of parameters which characterize both the $O_2$ transport capacity and the $O_2$ release capacity of human RBCs. The parameters of the $O_2$ transport capacity, i.e., Hb concentration, the number of RBCs, and hemocrit, are commonly used in clinical diagnosis. However, the equally important parameters of the $O_2$ release capacity, i.e., $O_2$ half-saturation pressure of Hb and RBCs, and the amounts of high and low oxygen affinity hemoglobins in RBCs, are not routinely determined and were not given serious consideration until pioneering work by Gerosonde and Nicolau (*Blut*, 1979, 39, 1–7).

In the 1980s, Nicolau et al. (*J. Appl. Physiol.* 58:1810–1817 (1985); "PHYTIC ACID: Chemsitry and Applications"; Graf, E., Ed.; Pilatus Press, Minneapolis, Minn., USA; 1986; and *Proc. Natl. Acad. Sci. USA* 1987, 84, 6894–6898) reported that the encapsulation in red blood cells (RBCs) of IHP, via a technique of controlled lysis and resealing, results in a significant decrease in the hemoglobin affinity for oxygen. The procedure yielded RBCs with unchanged life spans, normal ATP and K+ levels, and normal Theological competence. Enhancement of the $O_2$-release capacity of these cells brought about significant physiological effects in piglets: 1) reduced cardiac output, linearly dependent on the P50 value of the RBCs; 2) increased arteriovenous difference; and 3) improved tissue oxygenation. Long term experiments showed that in piglets the high $P_{50}$ value of IHP-RBCs was maintained over the entire life spans of the RBCs.

More recently, Nicolau et al. (*TRANSFUSION* 1995, 35, 478–486; and U.S. Pat. No. 5,612,207) reported the use of a large-volume, continuous-flow electroporation system for the encapsulating IHP in human RBCs. These modified RBCs possess $P_{50}$ values of approximately 50 torr, roughly twice that of unmodified human RBCs. Additionally, 85% of the RBCs survived the electroporation process, displaying hematologic indices nearly identical to those of unmodified RBCs. Nicolau's electroporation system processes one unit of blood every ninety minutes.

V. Specific Clinical Applications of Enhanced Oxygen Delivery

There are numerous clinical conditions that would benefit from treatments that would increase tissue delivery of oxygen bound to hemoglobin. For example, the leading cause of death in the United States today is cardiovascular disease. The acute symptoms and pathology of many cardiovascular diseases, including congestive heart failure, myocardial infarction, stroke, intermittent claudication, and sickle cell anemia, result from an insufficient supply of oxygen in fluids that bathe the tissues. Likewise, the acute loss of blood following hemorrhage, traumatic injury, or surgery results in decreased oxygen supply to vital organs. Without oxygen, tissues at sites distal to the heart, and even the heart itself, cannot produce enough energy to sustain their normal functions. The result of oxygen deprivation is tissue death and organ failure.

Although the attention of the American public has long been focused on the preventive measures required to alleviate heart disease, such as exercise, appropriate dietary habits, and moderation in alcohol consumption, deaths continue to occur at an alarming rate. Since death results from oxygen deprivation, which in turn results in tissue destruction and/or organ dysfunction, one approach to alleviate the life-threatening consequences of cardiovascular disease is to increase oxygenation of tissues during acute stress. The same approach is also appropriate for persons suffering from blood loss or chronic hypoxic disorders, such as congestive heart failure.

Another condition which could benefit from an increase in the delivery of oxygen to the tissues is anemia. A significant portion of hospital patients experience anemia or a low "crit" caused by an insufficient quantity of red blood cells or hemoglobin in their blood. This leads to inadequate oxygenation of their tissues and subsequent complications. Typically, a physician can temporarily correct this condition by transfusing the patient with units of packed red blood cells.

Enhanced blood oxygenation may also reduce the number of heterologous transfusions and allow use of autologous transfusions in more case. The current method for treatment of anemia or replacement of blood loss is transfusion of whole human blood. It is estimated that three to four million patients receive transfusions in the U.S. each year for surgical or medical needs. In situations where there is more time it is advantageous to completely avoid the use of donor or heterologous blood and instead use autologous blood.

Often the amount of blood which can be drawn and stored prior to surgery limits the use of autologous blood. Typically, a surgical patient does not have enough time to donate a sufficient quantity of blood prior to surgery. A surgeon would like to have several units of blood available. As each unit requires a period of several weeks between donations and can not be done less than two weeks prior to surgery, it is often impossible to sequester an adequate supply of blood. By processing autologous blood with IHP, less blood is required and it becomes possible to completely avoid the transfusion of heterologous blood.

Because IHP-treated RBCs may release up to 2–3 times as much oxygen as untreated red cells, in many cases, a physician will need to transfuse fewer units of IHP-treaded red cells. This exposes the patient to less heterologous blood, decreases the extent of exposure to vital diseases from blood donors and minimizes immune function disturbances secondary to transfusions. The ability to infuse more efficient red blood cells is also advantageous when the patients blood volume is excessive. In more severe cases, where oxygen transport is failing, the ability to improve rapidly a patient's tissue oxygenation is life saving.

Although it is evident that methods of enhancing oxygen delivery to tissues have potential medical applications, currently there are no methods clinically available for increasing tissue delivery of oxygen bound to hemoglobin. Transient, 6 to 12 hour elevations of oxygen deposition have been described in experimental animals using either DPG or molecules that are precursors of DPG. The natural regulation of DPG synthesis in vivo and its relatively short biological half-life, however, limit the DPG concentration and the duration of increased tissue $PO_2$, and thus limit its therapeutic usefulness.

Additionally, as reported in Genetic Engineering News, Vol. 12, No. 6, Apr. 15, 1992, several groups are attempting to engineer free oxygen-carrying hemoglobin as a replacement for human blood. Recombinant, genetically modified human hemoglobin that does not break down in the body and that can readily release up to 30% of its bound oxygen is currently being tested by Somatogen, Inc., of Boulder Colo. While this product could be useful as a replacement for blood lost in traumatic injury or surgery, it would not be effective to increase $PO_2$ levels in ischemic tissue, since its oxygen release capacity is equivalent to that of natural hemoglobin (27–30%). As are all recombinant products, this synthetic hemoglobin is also likely to be a costly therapeutic.

Synthetic human hemoglobin has also been produced in neonatal pigs by injection of human genes that control hemoglobin production. This product may be less expensive product than the Somatogen synthetic hemoglobin, but it does not solve problems with oxygen affinity and breakdown of hemoglobin in the body.

SUMMARY OF THE INVENTION

The present invention relates to compositions, and methods of use thereof, consisting essentially of aliphatic ammonium cations and inositol hexaphosphate (IHP), an allosteric effector of hemoglobin.

The aliphatic ammonium cation is substituted with one or more times with aliphatic groups, which can be the same or different. In certain embodiments, the aliphatic ammonium cation is a primary ammonium cation represented by the general formula $NH_3(R)$, wherein R is an aliphatic group, preferably an alkyl, more preferably a lower alkyl, i.e., a $C_1-C_6$ alkyl, and even more preferably a $C_3-C_6$ cycloalkyl. In certain preferred embodiments, the ammonium cation is preferably derived from cyclic amines.

In certain embodiments, the present invention relates to compounds, and compositions thereof, that deliver IHP into erythrocytes ex vivo, for lowering the oxygen affinity of hemoglobin in red blood cell suspensions and whole blood. It is an object of this invention to provide methods for delivering IHP into erythrocytes in whole blood, utilizing compounds, or compositions thereof, that do not lose their effectiveness in the presence of normal concentrations of the remaining components of whole blood.

In certain embodiments, the present invention relates to a method of treating a subject for any one or more diseases where an increase in oxygen delivery of hemoglobin would be of benefit comprising the steps of treating red blood cells or whole blood ex vivo with one or more compounds or compositions of the present invention, followed by suitably purifying said red blood cells or whole blood, and administering the thus prepared red blood cells or whole blood to said subject. By 'suitably purifying' it is meant a method of washing and separating, for example by centrifugation, the red blood cell- or whole blood-allosteric effector suspension and discarding the supernatant until no non-encapsulated allosteric effector can be detected. An exemplary method is presented in detail by Nicolau et al. in U.S. Pat. No. 5,612,207, which is incorporated by reference herein.

Ligands for the allosteric site of hemoglobin interact with the hemoglobin molecule and impact its ability to bind oxygen. This invention is particularly concerned with the delivery of IHP, causing oxygen to be bound relatively less tightly to hemoglobin, such that oxygen is off-loaded from the hemoglobin molecule more easily.

The process of allosterically modifying hemoglobin towards a lower oxygen affinity state in whole blood may be used in a wide variety of applications, including treatments for ischemia, heart disease, wound healing, radiation therapy of cancer, and adult respiratory distress syndrome (ARDS). Furthermore, a decrease in the oxygen affinity of hemoglobin in whole blood will extend its useful shelf-life vis-à-vis transfusions, and/or restore the oxygen carrying capacity of aged blood.

BRIEF DESCRIPTION OF THE FIGURES

FIG. 1 tabulates the names or structures of various ammonium salts of inositol hexaphosphate and the corresponding abbreviations used herein.

FIG. 2 tabulates the names or structures of various ammonium salts of inositol hexaphosphate and the corresponding abbreviations used herein.

FIG. 3 tabulates the names or structures of various ammonium salts of inositol hexaphosphate and the corresponding abbreviations used herein.

FIG. 4 tabulates the names, references, molecular formulas, and molecular weights of various cyclic primary ammonium salts of inositol hexaphosphate.

FIG. 5 tabulates the names, references, molecular formulas, and molecular weights of various amino acid and acyclic primary ammonium salts of inositol hexaphosphate.

FIG. 6 tabulates the names, references, molecular formulas, and molecular weights of various secondary ammonium salts of inositol hexaphosphate.

FIG. 7 tabulates the names, references, molecular formulas, and molecular weights of various tertiary ammonium salts of inositol hexaphosphate.

FIG. 8 tabulates the names, references, molecular formulas, and molecular weights of various diammonium salts of inositol hexaphosphate.

FIG. 9 tabulates the names, references, molecular formulas, and molecular weights of various tri- and tetra-ammonium salts of inositol hexaphosphate.

FIG. 10 tabulates the name, reference, molecular formula, and molecular weight of a hexa-ammonium salt of inositol hexaphosphate.

FIG. 11 depicts several ammonium salts of IHP and their corresponding $K_{ow}$ and $K_{os}$ partition coefficients.

FIG. 15 tabulates the $P_{50}$ values at various osmolarities of whole blood, and free hemoglobin that has been pre-incubated with various ammonium salts of inositol hexaphosphate.

FIG. 16 tabulates the $P_{50}$ values at various osmolarities of whole blood, and free hemoglobin that has been pre-incubated with various ammonium salts of inositol hexaphosphate.

FIG. 17 tabulates the $P_{50}$ values at various osmolarities of whole blood, and free hemoglobin that has been pre-incubated with various ammonium salts of inositol hexaphosphate.

FIG. 19 depicts several di-, tri-, and tetra-ammonium salts of IHP and their corresponding $K_{ow}$ and $K_{os}$ partition coefficients.

DETAILED DESCRIPTION OF THE INVENTION

I. Overview

Figure 12:
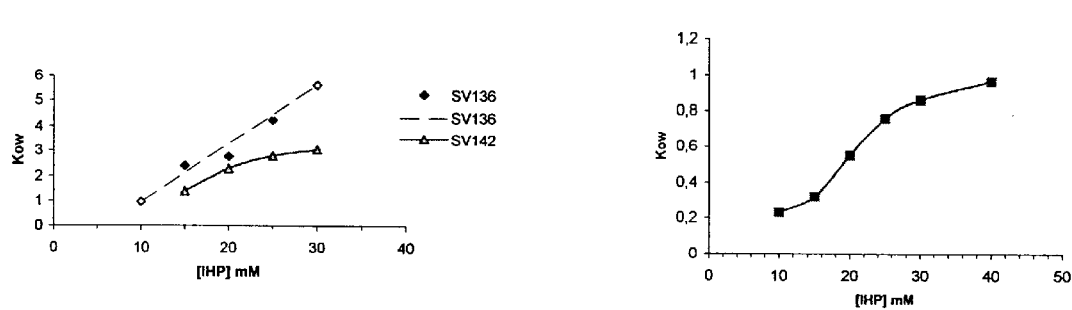
FIG. 12 compares $K_{ow}$ dependence on IHP starting concentration of the IHP salts, SV75 (9 cycloheptylammonium) and SV131 (11 cyclooctylammonium).

The process of allosterically modifying hemoglobin towards a low oxygen affinity state in whole blood could be used in a wide variety of applications including in treatments for ischemia, heart disease, complications associated with angioplasty, wound healing, radiation therapy of cancer, adult respiratory distress syndrome (ARDS), etc., in extending the shelf-life of blood or restoring the oxygen carrying capacity of out-dated blood, and as sensitizers for x-ray irradiation in cancer therapy, as well as in many other applications.

This invention is related to the use of allosteric hemoglobin modifier compounds in red blood cell suspensions, e.g., in whole blood. Serum albumin, which is the most abundant protein in blood plasma, has been identified as inhibiting the allosteric effects of clofibric acid, bezafibrate, and L3,5/L3, 4,5. The precise nature of this inhibition is not fully understood, but appears to be related to these compounds binding to the serum albumin. In contrast, the subject compounds have been found to be relatively unaffected by the presence of serum albumin. Ligands for the allosteric site of hemoglobin that are not adversely effected by serum albumin represent particularly good candidates for drug applications, since the performance of the drug will not be frustrated by the presence of serum albumin present in a patient's blood.

This invention relates to the incorporation of a wide variety of therapeutically useful substances into mammalian red blood cells (RBCs), which could not previously be accomplished without unacceptable losses of RBC contents and/or integrity. In particular, the compounds and methods of the present invention make possible the introduction or incorporation into RBCs of anionic agents, such as DNA, RNA, chemotherapeutic agents, and antibiotic agents. These and other water-soluble substances may be used for a desired slow continuous delivery or targeted delivery when the treated and purified RBC carrier is later injected in vivo. The particular anion or polyanion to be selected can be based on whether an allosteric effector of hemoglobin would be desirable for a particular treatment.

The present invention provides a novel method for increasing the oxygen-carrying capacity of erythrocytes. In accordance with the method of the present invention, the IHP combines with hemoglobin in a stable way, and shifts its oxygen releasing capacity. Erythrocytes with IHP-hemoglobin can release more oxygen per molecule than hemoglobin alone, and thus more oxygen is available to diffuse into tissues for each unit of blood that circulates. IHP is preferably added to red blood cells in vitro or ex vivo, as it appears that it is toxic to animals under certain circumstances.

Another advantage of IHP-treated red blood cells is that they show the Bohr effect in circulation and when stored. Normal red blood cells that have been stored do not regain their maximum oxygen carrying capacity in circulation for approximately 24 hours. This is because the DPG present in normal red blood cells is degraded by native enzymes, e.g., phosphatases, during storage and must be replaced by the body after transfusion. In contrast, red blood cells treated according to the present invention retain their maximum oxygen carrying capacity during storage and therefore can deliver oxygen to the tissues in response to demand immediately after transfusion into a human or animal because there are no native enzymes in erythrocytes which degrade IHP.

IHP-treated RBCs may be used in the treatment of acute and chronic conditions, including, but not limited to, hospitalized patients, cardiovascular operations, chronic anemia, anemia following major surgery, coronary infarction and associated problems, chronic pulmonary disease, cardiovascular patients, autologous transfusions, as an enhancement to packed red blood cells transfusion (hemorrhage, traumatic injury, or surgery) congestive heart failure, myocardial infarction (heart attack), stroke, peripheral vascular disease, intermittent claudication, circulatory shock, hemorrhagic shock, anemia and chronic hypoxia, respiratory alkalemia, metabolic alkalosis, sickle cell anemia, reduced lung capacity caused by pneumonia, surgery, complications associated with angioplasty, pneumonia, trauma, chest puncture, gangrene, anaerobic infections, blood vessel diseases such as diabetes, substitute or complement to treatment with hyperbaric pressure chambers, intra-operative red cell salvage, cardiac inadequacy, anoxia-secondary to chronic indication, organ transplant, carbon monoxide, nitric oxide, and cyanide poisoning.

This invention is related to a method of treating a subject for any one or more of the above diseases comprising the steps of treating red blood cells or whole blood ex vivo with one or more compounds or compositions of the present invention, followed by suitably purifying said red blood cells or whole blood, and administering the thus prepared red blood cells or whole blood to said subject. By 'suitably purifying' it is meant a method of washing and separating the red blood cell- or whole blood-allosteric effector suspension and discarding the supernatant until no non-encapsulated allosteric effector can be detected, e.g., as devised by Nicolau et al. in U.S. Pat. No. 5,612,207. Alternatively, a compound comprised of an allosteric effector can be administered directly to a subject if the compound does not have toxic effects in the subject, or at least its beneficial effects predominate over its toxicity in a subject. Toxicity of a compound in a subject can be determined according to methods known in the art.

Treating a human or animal for any one or more of the above disease states is done by transfusing into the human or animal between approximately 0.1 and 6 units (1 unit= 500 mL) of IHP-treated blood that has been prepared according to the present invention. In certain cases, blood exchange with IHP-treated blood may be possible. The volume of IHP-treated red blood cells that is administered to the human or animal will depend upon the value of $P_{50}$ for the IHP-treated RBCs. It is to be understood that the volume of IHP-treated red blood cells that is administered to the patient can vary and still be effective. IHP-treated RBCs are similar to normal red blood cells in every respect except that their $P_{50}$ value is shifted towards higher partial pressures of $O_2$. Erythrocytes release oxygen only in response to demand by organs and tissue. Therefore, the compounds, compositions thereof, and methods of the present invention will only restore a normal level of oxygenation to healthy tissue, avoiding the cellular damage that is associated with an over-abundance of oxygen.

Because the compounds, compositions, and methods of the present invention are capable of allosterically modifying hemoglobin to favor the low oxygen affinity "T" state (i.e., right shifting the equilibrium curve), RBC's or whole blood treated with the compounds of the present invention and subsequently purified will be useful in treating a variety of disease states in mammals, including humans, wherein tissues suffer from low oxygen tension, such as cancer and ischemia. Furthermore, as disclosed by Hirst et al. (*Radiat. Res.*, 112, (1987), pp. 164), decreasing the oxygen affinity of hemoglobin in circulating blood has been shown to be beneficial in the radiotherapy of tumors. RBC's or whole blood treated with the compounds of the present invention and subsequently purified may be administered to patients in whom the affinity of hemoglobin for oxygen is abnormally high. For example, certain hemoglobinopathies, certain respiratory distress syndromes, e.g., respiratory distress syndromes in new born infants aggravated by high fetal hemoglobin levels, and conditions in which the availability of hemoglobin/ oxygen to the tissues is decreased (e.g., in ischemic conditions such as peripheral vascular disease, coronary occlusion, cerebral vascular accidents, or tissue transplant). The compounds and compositions may also be used to inhibit platelet aggregation, antithrombotic purposes, and wound healing.

Additionally, the compounds and compositions of the present invention can be added to whole blood or packed cells preferably at the time of storage or at the time of transfusion in order to facilitate the dissociation of oxygen from hemoglobin and improve the oxygen delivering capability of the blood. When blood is stored, the hemoglobin in the blood tends to increase its affinity for oxygen by losing 2,3-diphosphoglycerides. As described above, the compounds and compositions of this invention are capable of reversing and/or preventing the functional abnormality of hemoglobin observed when whole blood or packed cells are stored. The compounds and compositions may be added to whole blood or red blood cell fractions in a closed system using an appropriate reservoir in which the compound or composition is placed prior to storage or which is present in the anticoagulating solution in the blood collecting bag.

Administration to a patient can be achieved by intravenous or intraperitoneal injection where the dose of treated red blood cells or whole blood and the dosing regiment is varied according to individual's sensitivity and the type of disease state being treated.

Solid tumors are oxygen deficient masses. The compounds, compositions and methods of this invention may be exploited to cause more oxygen to be delivered to tumors, increasing radical formation and thereby increasing tumor killing during radiation. In this context, such IHP-treated blood will only be used in conjunction with radiotherapy.

The compounds, compositions and methods of this invention may be exploited to cause more oxygen to be delivered at low blood flow and low temperatures, providing the ability to decrease or prevent the cellular damage, e.g., myocardial or neuronal, typically associated with these conditions.

The compounds, compositions and methods of this invention may be exploited to decrease the number of red blood cells required for treating hemorrhagic shock by increasing the efficiency with which they deliver oxygen.

Damaged tissues heal faster when there is better blood flow and increased oxygen tension. Therefore, the compounds, compositions and methods of this invention may be exploited to speed wound healing. Furthermore, by increasing oxygen delivery to wounded tissue, the compounds, compositions and methods of this invention may play a role in the destruction of infection causing bacteria at a wound.

The compounds, compositions and methods of this invention may be effective in enhancing the delivery oxygen to the brain, especially before complete occlusion and reperfusion injuries occur due to free radical formation. Furthermore, the compounds, compositions and methods of this invention of this invention should reduce the expansion of arterioles under both hypoxic and hypotensive conditions.

The compounds, compositions and methods of this invention of this invention should be capable of increasing oxygen delivery to blocked arteries and surrounding muscles and tissues, thereby relieving the distress of angina attacks.

Acute respiratory disease syndrome (ARDS) is characterized by interstitial and/or alveolar edema and hemorrhage as well as perivascular lung edema associated with the hyaline membrane, proliferation of collagen fibers, and swollen epithelium with increased pinocytosis. The enhanced oxygen delivering capacity provided to RBCs by the compounds, compositions and methods of this invention could be used in the treatment and prevention of ARDS by militating against lower than normal oxygen delivery to the lungs.

There are several aspects of cardiac bypass surgery that make attractive the use of compounds or compositions or methods of the present invention. First, the compounds and compositions of the present invention may act as neuroprotective agents. After cardiac bypass surgery, up to 50–70% of patients show some signs of cerebral ischemia based on tests of cognitive function. Up to 5% of these patients have evidence of stroke. Second, cardioplegia is the process of stopping the heart and protecting the heart from ischemia during heart surgery. Cardioplegia is performed by perfusing the coronary vessels with solutions of potassium chloride and bathing the heart in ice water. However, blood cardioplegia is also used. This is where potassium chloride is dissolved in blood instead of salt water. During surgery the heart is deprived of oxygen and the cold temperature helps slow down metabolism. Periodically during this process, the heart is perfused with the cardioplegia solution to wash out metabolites and reactive species. Cooling the blood increases the oxygen affinity of its hemoglobin, thus making oxygen unloading less efficient. However, treatment of blood cardioplegia with RBC's or whole blood previously treated with compounds or compositions of the present invention and subsequently purified will counteract the effects of cold on oxygen affinity and make oxygen release to the ischemic myocardium more efficient, possibly improving cardiac function after the heart begins to beat again. Third, during bypass surgery the patient's blood is diluted for the process of pump prime. This hemodilution is essentially acute anemia. Because the compounds and compositions of the present invention make oxygen transport more efficient, their use during hemodilution (whether in bypass surgery or other surgeries, such as orthopedic or vascular) would enhance oxygenation of the tissues in an otherwise compromised condition. Additionally, the compounds and methods of the present invention will also find use in patients undergoing angioplasty, who may experience acute ischemic insult, e.g., due to the dye(s) used in this procedure.

Additionally, microvascular insufficiency has been proposed by a number of investigators as a possible cause of diabetic neuropathy. The interest in microvascular derangement in diabetic neuropathic patients has arisen from studies suggesting that absolute or relative ischemia may exist in the nerves of diabetic subjects due to altered function of the endo- and/or epineurial blood vessels. Histopathologic studies have shown the presence of different degrees of endoneurial and epineurial microvasculopathy, mainly thickening of blood vessel wall or occlusion. A number of functional disturbances have also been demonstrated in the microvasculature of the nerves of diabetic subjects. Studies have demonstrated decreased neural blood flow, increased vascular resistance, decreased $pO_2$ and altered vascular permeability characteristics such as a loss of the anionic charge barrier and decreased charge selectivity. Abnormalities of cutaneous blood flow correlate with neuropathy, suggesting that there is a clinical counterpart to the microvascular insufficiency that may prove to be a simple non-invasive test of nerve fiber dysfunction. Accordingly, patients suffering from diabetic neuropathies and/or other neurodegenerative disorders will likely benefit from treatment based on the compounds and methods of the present invention.

Red blood cells or whole blood previously treated with the compounds of the present invention and subsequently suitably purified may be used to enhance oxygen delivery in any organism, e.g., fish, that uses a hemoglobin with an allosteric binding site.

II. Definitions

For convenience, certain terms employed in the specification, examples, and appended claims are collected here. As used throughout this specification and the claims, the following terms have the following meanings:

The term "hemoglobin" includes all naturally- and non-naturally-occurring hemoglobin.

The term "hemoglobin preparation" includes hemoglobin in a physiologically compatible carrier or lyophilized hemoglobin reconstituted with a physiologically compatible carrier, but does not include whole blood, red blood cells or packed red blood cells.

The term "toxic" refers to a property where the deleterious effects are greater than the beneficial effects.

The term "nontoxic" refers to a property where the beneficial effects are greater than the deleterious effects.

The term "whole blood" refers to blood containing all its natural constituents, components, or elements or a substantial amount of the natural constituents, components, or elements. For example, it is envisioned that some components may be removed by the purification process before administering the blood to a subject.

"Purified", "purification process", and "purify" all refer to a state or process of removing one or more compounds of the present invention from the red blood cells or whole blood such that when administered to a subject the red blood cells or whole blood is nontoxic.

"Non-naturally-occurring hemoglobin" includes synthetic hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, transgenic DNA technology, protein synthesis, and other mutation-inducing methods.

"Chemically-modified hemoglobin" is a natural or non-natural hemoglobin molecule which is bonded to another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin.

"Oxygen affinity" means the strength of binding of oxygen to a hemoglobin molecule. High oxygen affinity means hemoglobin does not readily release its bound oxygen molecules. The P50 is a measure of oxygen affinity.

"Cooperativity" refers to the sigmoidal oxygen-binding curve of hemoglobin, i.e., the binding of the first oxygen to one subunit within the tetrameric hemoglobin molecule enhances the binding of oxygen molecules to other unligated subunits. It is conveniently measured by the Hill coefficient (n[max]). For Hb A, n[max]=3.0.

The term "treatment" is intended to encompass also prophylaxis, therapy and cure.

"Ischemia" means a temporary or prolonged lack or reduction of oxygen supply to an organ or skeletal tissue. Ischemia can be induced when an organ is transplanted, or by conditions such as septic shock and sickle cell anemia.

"Skeletal tissue" means the substance of an organic body of a skeletal organism consisting of cells and intercellular material, including but not limited to epithelium, the connective tissues (including blood, bone and cartilage), muscle tissue, and nerve tissue.

"Ischemic insult" means damage to an organ or skeletal tissue caused by ischemia.

"Subject" means any living organism, including humans, and mammals.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

As used herein, the term "surgery" refers to the treatment of diseases, injuries, and deformities by manual or operative methods. Common surgical procedures include, but are not limited to, abdominal, aural, bench, cardiac, cineplastic, conservative, cosmetic, cytoreductive, dental, dentofacial, general, major, minor, Moh's, open heart, organ transplantation, orthopedic, plastic, psychiatric, radical, reconstructive, sonic, stereotactic, structural, thoracic, and veterinary surgery. The method of the present invention is suitable for patients that are to undergo any type of surgery dealing with any portion of the body, including but not limited to those described above, as well as any type of any general, major, minor, or minimal invasive surgery.

"Minimally invasive surgery" involves puncture or incision of the skin, or insertion of an instrument or foreign material into the body. Non-limiting examples of minimal invasive surgery include arterial or venous catheterization, transurethral resection, endoscopy (e.g., laparoscopy, bronchoscopy, uroscopy, pharyngoscopy, cystoscopy, hysteroscopy, gastroscopy, coloscopy, colposcopy, celioscopy, sigmoidoscopy, and orthoscopy), and angioplasty (e.g., balloon angioplasty, laser angioplasty, and percutaneous transluminal angioplasty).

The term "$ED_{50}$" means the dose of a drug that produces 50% of its maximum response or effect. Alternatively, the dose that produces a pre-determined response in 50% of test subjects or preparations.

The term "$LD_{50}$" means the dose of a drug that is lethal in 50% of test subjects.

The term "therapeutic index" refers to the therapeutic index of a drug defined as $LD_{50}/ED_{50}$.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "structure-activity relationship (SAR)" refers to the way in which altering the molecular structure of drugs alters their interaction with a receptor, enzyme, etc.

The term "ammonium cation" refers to the structure below:

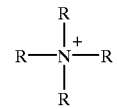

wherein R represents independently for each occurrence H or a substituted or unsubstituted aliphatic group. An "aliphatic ammonium cation" refers to the above structure when at least one R is an aliphatic group. A "quaternary ammonium cation" refers to the above structure when all four occurrences of R independently represent aliphatic groups. R can be the same for two or more occurrences, or different for all four.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl; a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

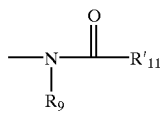

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

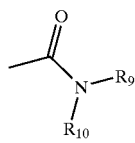

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

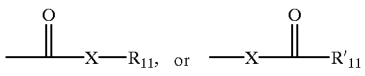

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

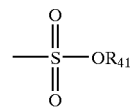

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

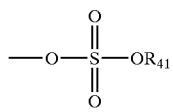

in which R$_{41}$ is as defined above.

The term "sulfonamido" is art recognized and includes a moiety that can be represented by the general formula:

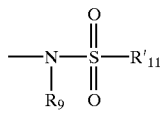

in which R$_9$ and R'$_{11}$ are as defined above.

The term "sulfamoyl" is art-recognized and includes a moiety that can be represented by the general formula:

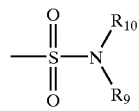

in which R$_9$ and R$_{10}$ are as defined above.

The term "sulfonyl", as used herein, refers to a moiety that can be represented by the general formula:

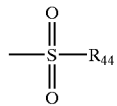

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

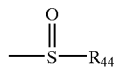

in which R$_{44}$ is selected from the group consisting of hydrogen, alkyl, alkenyl, alkynyl, cycloalkyl, heterocyclyl, aralkyl, or aryl.

A "phosphoryl" can in general be represented by the formula:

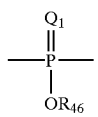

wherein Q$_1$ represented S or O, and R$_{46}$ represents hydrogen, a lower alkyl or an aryl. When used to substitute, e.g., an alkyl, the phosphoryl group of the phosphorylalkyl can be represented by the general formula:

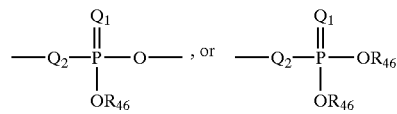

wherein Q$_1$ represented S or O, and each R$_{46}$ independently represents hydrogen, a lower alkyl or an aryl, Q$_2$ represents O, S or N. When Q$_1$ is an S, the phosphoryl moiety is a "phosphorothioate".

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Compounds of the Invention

Several years ago, it was discovered that the antilipidemic drug clofibric acid lowered the oxygen affinity of hemoglobin solutions (Abraham et al., *J. Med. Chem.* 25, 1015 (1982), and Abraham et al., *Proc. Natl. Acad. Sci. USA* 80, 324 (1983)). Bezafibrate, another antilipidemic drug, was later found to be much more effective in lowering the oxygen affinity of hemoglobin solutions and suspensions of fresh, intact red cells (Perutz et al., *Lancet*, 881, Oct. 15, 1983). Subsequently, X-ray crystallographic studies have demonstrated that clofibric acid and bezafibrate bind to the same sites in the central water cavity of deoxyhemoglobin, and that one bezafibrate molecule will span the sites occupied by two clofibric acid molecules. Bezafibrate and clofibric acid act by stabilizing the deoxy structure of hemoglobin, shifting the allosteric equilibrium toward the low affinity deoxy form. Bezafibrate and clofibric acid do not bind in any specific manner to either oxy- or carbon-monoxyhemoglobin.

In later investigations, a series of urea derivatives [2-[4-[[(arylamino)carbonyl]-amino]phenoxy]-2-methylpropionic acids] was discovered that has greater allosteric potency than bezafibrate at stabilizing the deoxy structure of hemoglobin and shifting the allosteric equilibrium toward the low oxygen affinity form (Lalezari, Proc. Natl. Acad. Sci. USA 85, 6117 (1988)).

It has been determined that certain allosteric hemoglobin modifier compounds are hydrophobic molecules that can be bound to the body's neutral fat deposits and lipophilic receptors sites, thus lowering their potency due to a decreased concentration in RBCs. Administration of a hydrophobic compound, such as a mixture of anesthetic molecules, will saturate the body's neutral fat deposits and lipophilic receptor sites, and thereby increase the concentration of this type of allosteric modifiers in RBCs, where higher concentrations of effector will increase its ability to interact with hemoglobin, causing delivery of more oxygen.

Ligands for the allosteric site of hemoglobin, also known as allosteric effectors of hemoglobin, include 2,3-diphosphoglycerate (DPG), inositol hexakisphosphate (IHP), bezafibrate (Bzf), LR16 and L35 (two recently synthesized derivatives of Bzf), and pyridoxal phosphate. Additionally, hemoglobin's affinity for oxygen can be modulated through electrostatic interactions with chloride and/or organophosphate anions present in RBCs. These effectors, which bind preferentially to the deoxy-Hb tetramers at a distance from the heme groups, play a major role in the adaptation of the respiratory properties of hemoglobin to either allometric-dependent oxygen needs or to various hypoxic environments. Additionally, protons and carbon dioxide are physiological regulators for the oxygen affinity of hemoglobin. The heterotropic allosteric interaction between the non-heme ligands and oxygen, collectively called the Bohr effect, facilitates not only the transport of oxygen but also the exchange of carbon dioxide.

The present invention relates to compositions, and methods of use thereof, consisting essentially of a nontoxic ammonia cation (preferably water-soluble), and inositol hexaphosphate (IHP). In certain embodiments, the nontoxic ammonium cation is represented by the general formula $N(R)_4$, wherein R is, independently for each occurrence, H or an aliphatic group, which aliphatic group is preferably an alkyl, more preferably a lower (C1–C6) alkyl, and even more preferably a C1–C10 cyclic alkyl. In certain preferred embodiments, the ammonium cation is preferably derived from cyclic organic bases.

In certain embodiments, the present invention is related to compounds, and compositions thereof, which deliver IHP into erythrocytes ex vivo. Additionally, the invention is directed to the use of the compounds or compositions thereof that are effective in delivering IHP into erythrocytes, lowering the oxygen affinity state in red blood cell suspensions and whole blood. It is an object of this invention to provide methods for delivering IHP into erythrocytes in whole blood, utilizing compounds or compositions thereof that do not lose their effectiveness in the presence of normal concentrations of the remaining components of whole blood.

In certain embodiments, the present invention is related to a method of treating red blood cells or whole blood ex vivo with one or more nontoxic compounds or compositions of the present invention, suitably purifying said red blood cells or whole blood, and administering said purified red blood cells or whole blood to a subject for any treatment where an increase in oxygen delivery by hemoglobin would be a benefit.

In part, the present invention is directed toward the design of water-soluble membrane compatible molecules comprising ammonium cationic moieties, e.g., lipophilic ammonium groups. These molecules form complexes with IHP; such complexes are useful for the deliver of IHP into the cytoplasm of erythrocytes.

The ammonium group of the cationic component of the compounds of the present invention is particularly well suited for interaction with the phosphate residues of IHP and congeners thereof because of the coulombic interactions, i.e., the attraction between opposite charges, that can be established between the two moieties. We report here the use of ammonium salts for the efficient delivery of IHP into mammalian erythrocytes. Our data demonstrate the usefulness, convenience, and versatility of ammonium salts for delivery of IHP into the cytoplasm of mammalian cells.

In certain embodiments, the compounds of the present invention are represented by generalized structure 1:

wherein nC⁺ represents nona-cyclohexylammonium-tri-sodium, bis-dicyclohexylammonium-deca-sodium, octa-dicyclohexylammonium, hepta-1-aza-3-hydroxyl-bicyclo[2.2.2]cyclooctanium, dodeca-1-aza-3-hydroxyl-bicyclo[2.2.2]cyclooctanium, nona-piperidinium, penta-H₃N-Phe-OMe, nona-H₃N-Phe-OMe, hexa-1-indanylammonium, hepta-2-norbornylammonium, nona-decahydroquinolinium, hepta-H₃N-Phe-OEt, hexa-H₃N-Phe-OEt, octa-H₃N-sec-Leu-Ot-Bu, dodeca-diisopropylammonium, octa-H₃N-Pro-Ot-Bu, deca-H₃N-Tyr-OEt, tetra-cyclohexyl-1,2-bis-ammonium, nona-cycloheptylammonium, undecacyclopentylammonium, undecacyclohexylammonium, penta-(N,N'-dibenzyl)-ethylenediammonium, octa menthyl-1,8-diammonium, penta cyclohexyl-(1,3-bismethylammonium), penta (±)-(1,2-trans-diphenyl)-ethylenediammonium, nona N-cyclohexyl-piperidinium, bis (N¹,N³-cyclohexyl)-dipropylenetriammonium, tris tri-(N-cyclohexyl-2-amino-ethyl)-ammonium, tetra N,N'-di-(3-(N-cyclohexyl-amino)-propyl)-piperazinium, tris tri-(N-cycloheptyl-2-amino-ethyl)-ammonium, tri N,N'-di-(3-(N-cyclooctyl-amino)-propyl)-piperazinium, or bis N,N',N'',N'''-tetrahexyl-cyclam; and Aⁿ⁻ represents a conjugate base of inositol hexaphosphate, wherein n equals the number of cations comprised by nC⁺.

In certain embodiments, the present invention relates to a pharmaceutical composition, comprising a nontoxic compound of the present invention; and a pharmaceutically acceptable excipient.

IV. IHP-ammonium salts Preparation

IHP ammonium salts can be efficiently prepared from IHP, dodecasodium form and the corresponding free amine. IHP is first protonated using a cation-exchange resin and is mixed to an ethanolic solution of the desired amine. A first library of IHP-ammonium salts was thus generated from commercially available amines. The purpose was to assess the ability of amines to transport IHP into a 1-octanol phase ($K_{ow}$ measurements) or across erythrocyte membrane ($P_{50}$ shift) as a function of the amine structure. Therefore, we prepared IHP associated to primary, secondary and tertiary amines bearing alkyl-, cycloalkyl- and aromatic groups. In FIGS. 1–10 are represented the structures of the amines and the ammonium salts of inositol hexaphosphate constituting the present invention. FIGS. 1–7 depict monoamines and monoammonium salts, and FIGS. 8–10 depict the polyammonium salts.

V. Partition Coefficients of IHP-ammoniums Derivatives

Partition coefficients relate to the distribution of a solute between two immiscible liquid phases and are defined as the ratios of concentrations (or molar fraction) of the distributed solute. These data have been used to predict or rationalize numerous drug properties such as quantitative structure/activity relationship (C. Hansch, A. Leo *Exploring QSAR; Fundamentals and Applications in Chemistry and Biology*, Washington D.C., 1995), lipophilicity (J. Balzarini, M. Cools, E. D. Clercq *Bioch. Biophys. Res Comm.* 1986, 26, 6701–05) and pharmacokinetic characteristics. 1-Octanol has been found to properly mimic biological membranes, and it has been estimated than 1-octanol/water ($K_{ow}$) partition coefficients of more than 18 000 substances are now available in the literature (J. Sangster *Octanol/Water Partition Coefficients: Fundamentals and Physical Chemistry*, Chichester, 1997).

$$K_{ow} = \frac{[IHP]_{octanol}}{[IHP]_{water}}$$

Partition coefficients measurements. We synthesized a first series of IHP derivatives, ionically associated to different aliphatic and aromatic amines as well as amino-esters. Taking advantage of the 6 phosphate groups present in the IHP molecule, we measured, by ³¹P-NMR, the partition coefficients of IHP salts between a 1-octanol phase and two different aqueous phases: water and human serum. In FIG. 11 are represented the structures of the different amines preassociated to IHP and the corresponding partition coefficients $K_{ow}$ and $K_{os}$. These coefficients are measured after equilibration, at a concentration of 30 mM, close to the typical concentration employed for the biological evaluations (the standard concentration used for O₂-dissociation curve measurements is 22 mM).

Choice of the aqueous phases. Because of the plethora of comparable data described in the literature we first measured 1-octanol/water partition coefficients $K_{ow}$. To be even closer to physiological conditions, we pushed this investigation further by measuring 1-octanol/human serum partition coefficients $K_{os}$. Interestingly, we observed that $K_{os}$ values are systematically lower (by a factor of 2 to 5) than $K_{ow}$ values. Therefore, we only measured $K_{os}$'s when $K_{ow}$ values were significant. To illustrate this observation we compared the partitions of 2 IHP derivatives, SV75 and SV131, in different aqueous systems: water, artificial serum (for its composition, see the Experimental section) without and with albumin, and human serum. Table 1 summarizes these results.

TABLE 1

Partition coefficients (at 18 mM) of SV75 and SV131 with different aqueous phases.

| | $K_{ow}$ (water) | $K_{oa}$ (artificial serum without albumin) | $K_{oas}$ (artificial serum with albumin) | $K_{os}$ (human serum) |
|---|---|---|---|---|
| IHP, 9 | 0.411 | 0.088 | 0.041 | 0.031 |

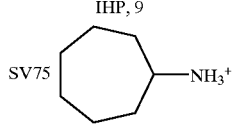

TABLE 1-continued

Partition coefficients (at 18 mM) of SV75 and SV131 with different aqueous phases.

| | $K_{ow}$ (water) | $K_{oa}$ (artificial serum without albumin) | $K_{oas}$ (artificial serum with albumin) | $K_{os}$ (human serum) |
|---|---|---|---|---|
| IHP, 11 | 8.98 | 2.16 | 1.81 | 1.85 |

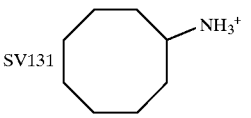

This simple series of results emphasizes the problems that can be encountered when experiments are lead from water to real physiological conditions. These results show the role that proteins present in serum, such as albumin, can play: they suggest that albumin is able to bind lipophilic amines, thus preventing IHP uptake into the octanolic phase. This conclusion is in accordance with the results published by Rim et al., who described a comparative study between octanol/water an octanol/buffer partition coefficients and correlated them to diffusion across brain microvessel endothelium (S. Rim, K. L. Audus, R. T. Borchardt *Int. J. Pharm.* 1986, 3, 79–84). Furthermore, albumin has been shown to participate to cholesterol transport in blood, thus demonstrating its ability to bind lipophilic compounds.

The analysis of this first series of partition coefficients can already lead to interesting conclusions. Cyclic aliphatic amines seem to display the best characteristics with regard to both lipophilicity and water solubility. Indeed, we observed a very significant increase in the $K_{ow}$ values from cyclopentyl-($<10^{-3}$) to cyclooctyl-ammoniums (9.98). Furthermore, the IHP cyclooctylammonium salt is still reasonably soluble in water (the aqueous solubility limit is between 25 and 30 mM), whereas the corresponding n-octylammonium IHP salt presents a solubility limit below 1 mM (thus rendering impossible its $K_{ow}$ measurement as well as its biological evaluation as a soluble drug). Hydrophobic amino-acids, even esterified, do not possess satisfactory transport properties into the octanol phase, and will not be considered as suitable lead compounds for further studies aiming to IHP delivery into red blood cells.

As a comparison, the octanol/buffer partition coefficient of AZT, an orally available anti-HIV drug has been determined to be 1.26 (the buffer being 100 mM sodium phosphate, pH 7.0) (T. P. Zimmerman, W. Mahony K. L. Prus *J. Biol. Chem.* 1987, 262, 5748–54). The same authors have shown that AZT diffuses across cell membranes independently of the nucleoside transport system.

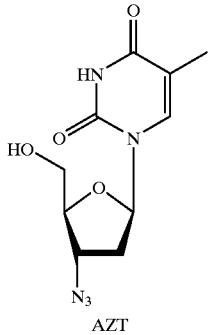

| | AZT | Thymidine |
|---|---|---|
| Octanol/buffer partition coefficient: | 1.26 | 0.064 |

The comparison between AZT $K_{ow}$ value and the best values we obtained suggests that, at a concentration of 30 mM, the lipophilicity of IHP-cycloalkylammoniums (especially cycloheptyl- and cyclooctylammoniums) should be sufficient to allow IHP to be delivered inside the erythrocyte.

However, new questions arise from this first study: the importance of the number of lipophilic amines associated to IHP and the evolution of IHP distribution in apolar phases as a function of the drug concentration.

$K_{ow}$ dependence on IHP starting concentration. To answer these important questions, we measured $K_{ow}$ variations of the two best IHP salts, SV75 (9 cycloheptylammonium) and SV131 (11 cyclooctylammonium). The resulting curves are depicted in FIG. 12. In all the aqueous phases tested, the variation of IHP partitioning as a function of the starting concentration is always the same: the distribution of IHP salts in octanol increases with the concentration. It should be noticed that even at a concentration of 10 mM, IHP-cyclooctylammonium is equally distributed in the serum and the octanol phase.

Figure 13:
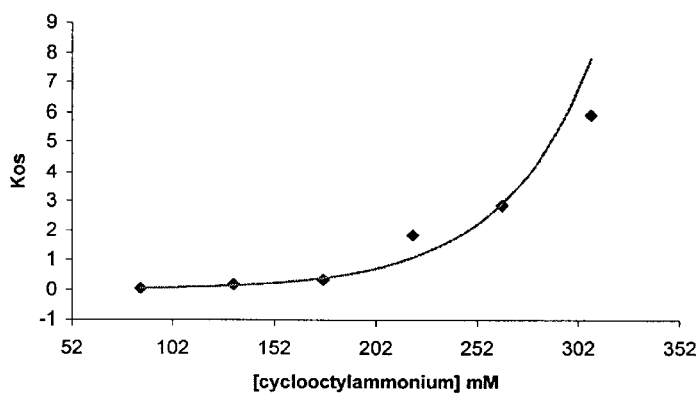
FIG. 13 depicts $K_{os}$ variation as a function of cyclooctylammonium concentration.

$K_{os}$ variation as a function of cyclooctylammonium concentration. FIG. 13 shows two important characteristics of the IHP transport into an apolar phase: at a constant IHP concentration (22 mM), 8 equivalents of cyclooctylammoniums are required to reach a $K_{os}$ value equal to 1, corresponding to an identical distribution between human serum and octanol. Secondly, this experiment shows that cyclooctylammonium ions, initially present in their hydrochloride form in the organic phase, are able to extract IHP, exclusively present as a sodium salt in human serum at the beginning of the experiment.

This remarkable behavior suggests that, even if they are accumulated in a cell membrane, transport molecules based on lipophilic amines could continue to extract polyphosphates.

From a therapeutic point of view, if one wishes to perform intravenous injection of highly concentrated IHP ammoniums salts, the biocompatibility of the transport molecule has to be seriously considered. Indeed, each IHP molecule is associated at least to 7 ammoniums, which means that the blood concentration in alkyl-ammonium will be at least seven times greater than IHP concentration. Consequently, the toxicity of the transport molecule becomes a major issue. Therefore, the next step of this work is the synthesis of polyamines bearing cycloalkyl groups. Once complexed to IHP, the ammoniums should reach a greater affinity for IHP ex vivo, and would provide a better delivery system.

VI. Biological Evaluation of the First Library

Figure 14:
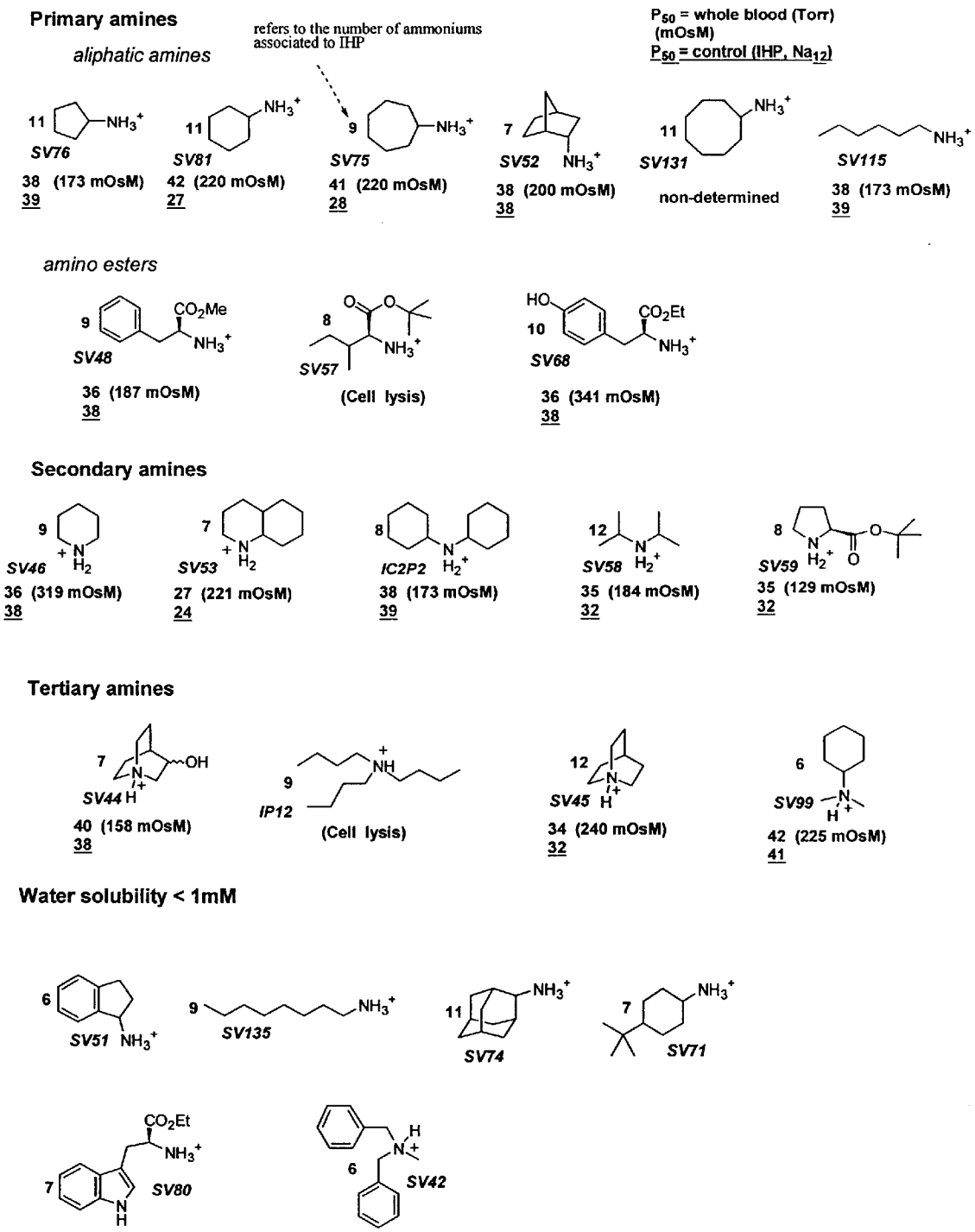
FIG. 14 depicts different IHP derivatives classified by ammonium types, the number of cations per IHP molecule as well as the reference number. The $P_{50}$ shift values are compared to the control experiment (underlined), corresponding to a test performed under the same conditions but with IHP in sodium form.

In FIG. 14 the different IHP derivatives have been classified by amine types, the number of cations per IHP molecule as well as the reference number are indicated beside each amine drawings. The $P_{50}$ shift values have to be compared to the control experiment (underlined), corresponding to a test performed in the same conditions but with IHP, sodium form. $P_{50}$ values have been measured in Professor Nicolau's laboratory in Boston (bioassay conditions: 75 µl of whole blood was incubated 2 minutes with 300 µl of a 50 mM solution of IHP derivatives. The system was then washed and 20 µl were used for measurement of the Hb-$O_2$ dissociation curve at 37° C.). See also FIGS. 15–17 for tables of $P_{50}$ values at various osmolarities of whole blood, and free hemoglobin that has been pre-incubated with various ammonium salts of inositol hexaphosphate.

From the biological evaluation described above, several conclusions can be drawn: the best results were obtained with two IHP-cycloalkylamines SV81 (undeca cyclohexyl-ammonium) and SV75 (nona cycloheptyl-ammonium), at 220 mOsM, these IHP salts triggered a 50% shift of the $P_{50}$ value (compared to the control experiment); aromatic (except tyrosine and phenylalanine derivatives) and acyclic aliphatic amines (with a chain length superior to 6 carbon atoms) decrease IHP solubility in aqueous media to such an extent that their biological activity could not be evaluated; amino-esters did not display transport properties; and tributyl-ammonium salts and isoleucine-tBu ester provoked a fast hemolysis of red blood cells, acting as strong detergents.

It is interesting to notice that good correlations between the biophysical study (1-octanol/serum partition coefficients) and the biological evaluation ($P_{50}$ shift measurements), since both techniques lead to the conclusion that cycloalkylamines displayed the best properties for both lipophilicity (transport across the erythrocyte membrane) and water solubility (which is an important parameter for the bioavailibility of a potential drug).

VII. Polyamine Synthesis

The biological tests performed on whole blood as well as the 1-octanol/water partition measurements showed that amines bearing cycloalkyl groups display the best properties in view of IHP delivery into red blood cells. Multiple interactions between a poly-anionic drug and a single transport molecule will increase the binding strength between the two partners, thus preventing the exchange, under physiological conditions with other cations present in high concentration in serum. For this reason, lipophilic polyamines seem to be the best candidates for transporting polyphosphates, such as IHP or DPG, across non-polar biological membranes. Thus, we optimized two general synthetic procedures in order to obtain a new series of polyamines bearing cycloalkyl groups: a reductive amination procedure leading to acyclic tetra-amines, and a coupled acylation/borane-reduction procedure for the preparation of macrocyclic polyamines.

The first optimized procedure lies on a single-step strategy, based on a reductive amination between primary amines and different cyclic ketones (Scheme 1).

Scheme 1
Poly-(cycloalkyl-amines) obtained by reductive amination.

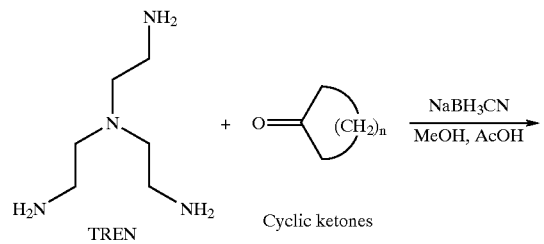

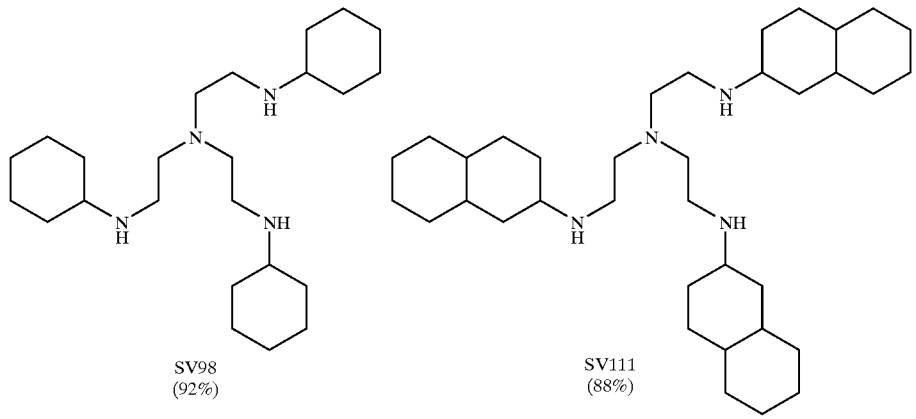
SV98 (92%)　　SV111 (88%)
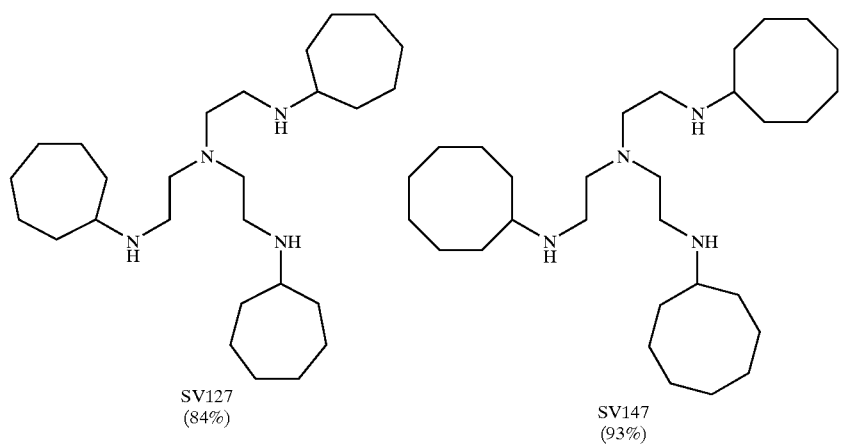
SV127 (84%)　　SV147 (93%)
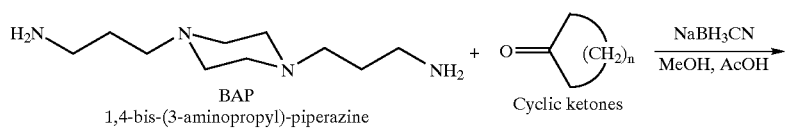
BAP
1,4-bis-(3-aminopropyl)-piperazine　　Cyclic ketones
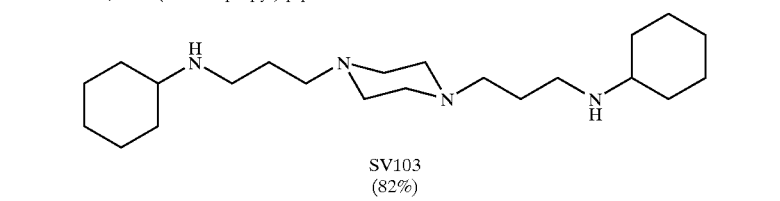
SV103 (82%)
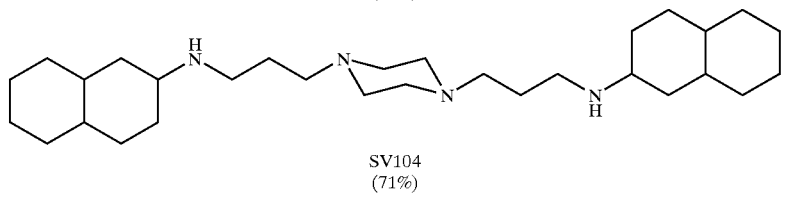
SV104 (71%)
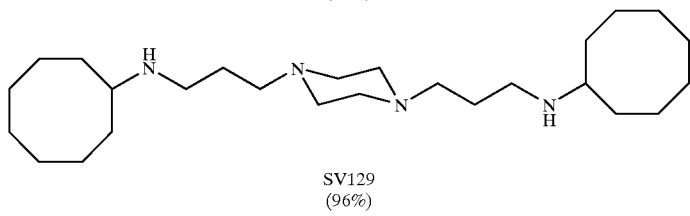
SV129 (96%)

This procedure proved efficient, giving good to excellent yields, and versatile enough to allow reactions with hindered ketones such as 2-decalone. The two central tetra-amine cores employed are TREN (tris-(2-aminoethy)-amine) and BAP (N,N'-bis-(3-aminopropyl)-piperazine). BAP is a linear tetra-amine presenting two primary amines susceptible to be alkylated, whereas TREN is a "ramified" molecule giving three possible N-alkylation sites through reductive amination. Consequently, seven new polyamines were obtained from these two central cores, either with cyclohexyl groups (compounds SV98 and SV103), cycloheptyl group (SV127), cyclooctyl-(SV147 and SV129), or 2-decalinyl groups (SV104 and SV111).

Figure 18:
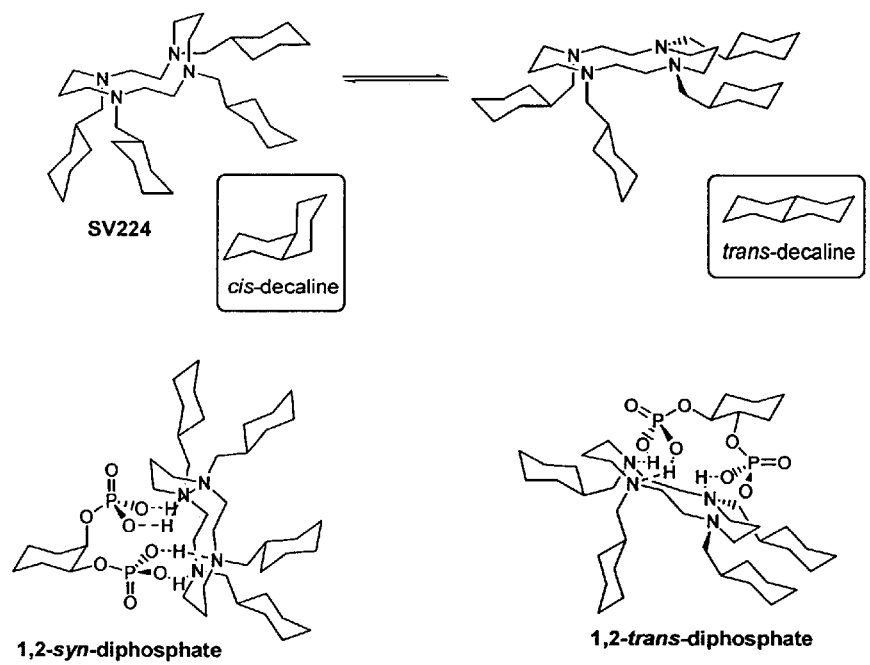
FIG. 18 depicts how CYCLAM, in a cis- or trans-decaline conformation may tightly bind 1,2-syn- or 1,2-trans-diphosphates.

We then prepared a series of lipophilic polyamines derived from CYCLAM, a well-studied and commercially available 14-membered ring tetra-aza macrocycle. Macrocycles were chosen to strengthen the interactions between polyphosphates and the poly-amine. To illustrate this idea, FIG. 18 shows how CYCLAM, in a cis- or a trans-decaline conformation may tightly bind 1,2-syn- or 1,2-trans-diphosphates, respectively.

One of the best procedures to obtain tetra-N-alkyl-cyclam derivatives consists in a per-acylation of the four secondary amines of cyclam, followed by reduction of the resulting tetra-amide using an excess of borane-THF complex (Scheme 2).

Scheme 2

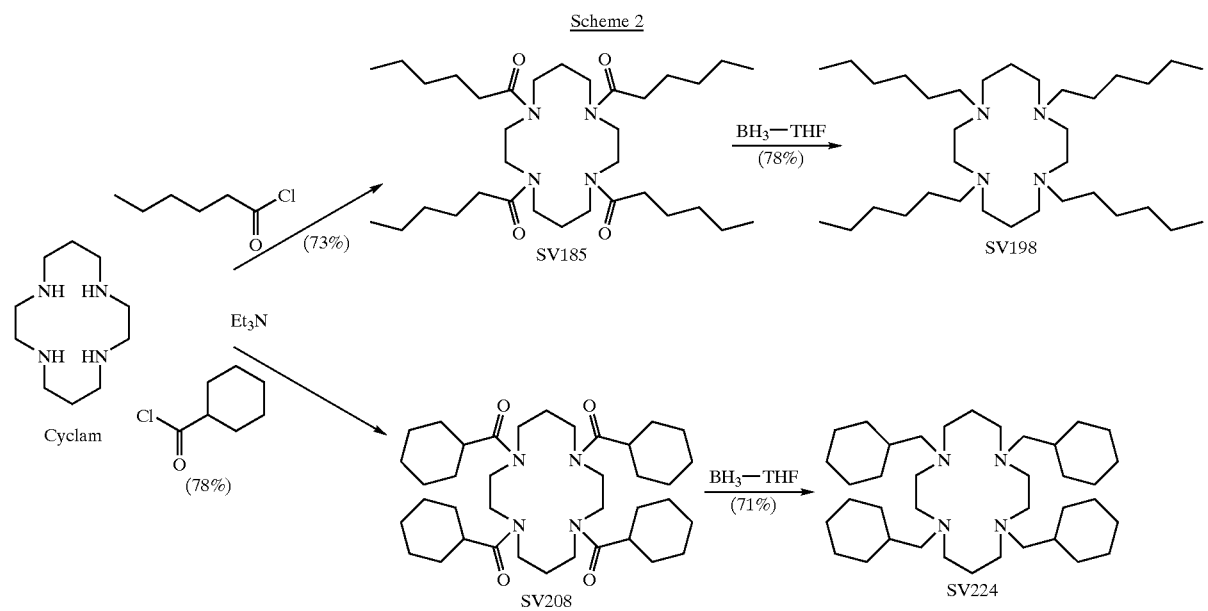

Thus, the cyclam derivatives SV198 and SV224 were generated. Taking into account the lack of solubility of IHP n-octylammonium salts in water, we chose to introduce shorter chains, n-hexyl lipophilic groups, for compound SV198. Compound SV224, with four methyl-cyclohexyl groups, was designed to prevent water solubility problems, and to insure a good partitionning into the apolar phase.

Partition coefficient of IHP associated with polyamines. A second library composed of di-, tri- and tetra-amines has been synthesized using standard procedures and complexed to IHP. The structures are listed in FIG. 19. Then, the partition coefficients $K_{ow}$ and $K_{os}$ were measured by $^{31}$P-NMR. Table 2 tabulates $P_{50}$ values measured with whole blood in the presence of the IHP/polyammonium salts.

TABLE 2

$P_{50}$ values measured with whole blood in the presence of IHP/polyammonium salts.

| NAME EFFECTOR (EFF) | | P50 CONTROL mmHg WB | P50 mmHg EFF:WB | pH/37° C. P50 Measure HemoxAnalyzer Hemox+ EFF:washed RBC | Osmolality of Effector (220–240) mOsM | RATIOS * EFF:WB |
|---|---|---|---|---|---|---|
| SV 89 | | | | | | |
| | fHb | 16 | 41.7 | 7.2–7.3 | Insoluble | 0.25 umoles EFF |
| SV 92 | | | | | | |
| | fHb | 16 | 45.0 | | | 0.25 umoles EFF |
| | WB | 41.4 | 58.5 | 7.2–7.3 | 84 | 1:0.375 |
| | WB | 40.5 | 38.7 | 7.2–7.3 | 336 | 1:1.5 |
| SV 94 | | | | | | |
| | fHb | 16 | 41.0 | 7.2–7.3 | Insoluble | 0.25 umoles EFF |
| SV 95 | | Insufficient Amount | | | | |
| SV 97 | | | | | | |
| | fHb | 16 | 46.7 | 7.2–7.3 | | 0.25 umoles EFF |
| | WB | 41.5 | 49.7 | 7.2–7.3 | 111 | 1:0.375 |
| | WB | 40.5 | 40.0 | 7.2–7.3 | 343 | 1:1.5 |
| SV102 | | | | | | |
| | fH | 16 | 41.0 | 7.2–7.3 | | 0.25 umoles EFF |
| | WB | 41.5 | 75.0 | 7.2–7.3 | 82 | 1:0.375 |
| | WB | 40.5 | 39.5 | 7.2–7.3 | 321 | 1:1.5 |
| SV106/108 | | | | | | |
| | WB Standard Wash (−C) | 26 | | | | |
| | WB | 29.5 | 33.4 | 7.2–7.3 | 151 | 1:0.375 |
| | WB | 29.5 | 26.3 | 7.2–7.3 | 345 | 1:0.375 |
| SV137 | | | | | | |
| | WB | 29.5 | 32.0 | 7.2–7.3 | 268 | 1:0.375 |
| | Insufficient amount | | | | | |
| SV141 | | | | | | |
| | fHb | 10.5 | 22.0 | 7.1–7.2 | | 1: 1(2.5 mM:2.5 mM) |
| | WB Standard Wash (−C) | 23.5 | | 7.1–7.2 | | 1:1.5 |
| | WB | Lyses | no sufficient RBC pellet | | | 1:0.375 |
| | WB | 25 | 25.0 | 7.1–7.2 | 221 | 1:1.5 | fHb = Free Hemoglobin
WB = Whole Blood

Figure 20:
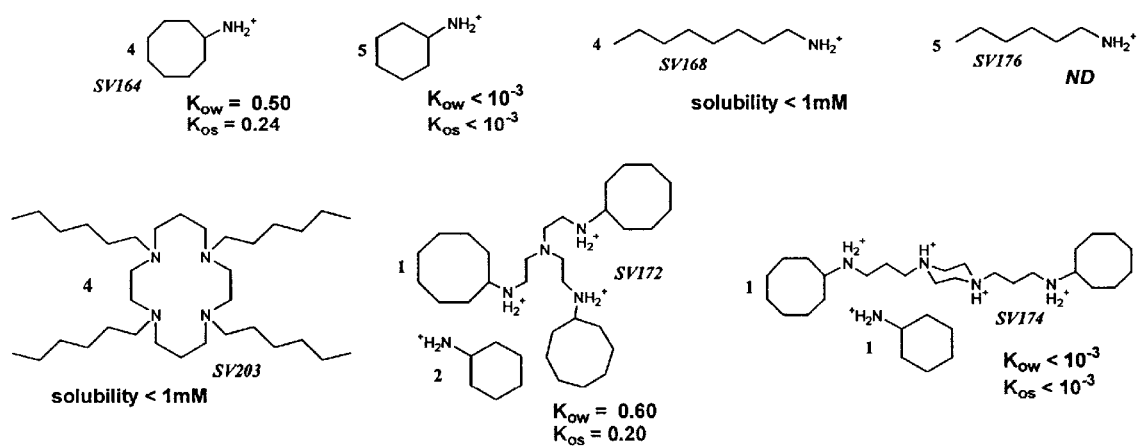
FIG. 20 depicts the structures of DPG salts of various ammonium ions and their 1-octanol/water and 1-octanol/serum partition coefficients.

Once again, the poly-cycloalkylamines displayed better properties than aromatic or acycic aliphatic ones. The tris-cycloheptyl-TREN associated to IHP (SV137) showed the best partitioning characteristics with $K_{ow}$=2.70 and $K_{os}$=0.64. Disappointingly, a polyethyleneimine bearing cyclohexyl groups on each primary amines once complexed to IHP gave a totally insoluble product in both aqueous and organic solutions. At first sight, TREN derivatives seem to be the best candidates for improving IHP transport. The biological evaluation of this new library is still in progress. Biophysical and biological properties of DPG-Polyamine salts. In order to compare the biophysical and the transport properties of polyamines associated to another polyphosphate other than IHP, we prepared poly-ammonium salts of the natural hemoglobin effector, 2,3-diphospho-glycerate (DPG). We selected, from the 2 IHP libraries, the best amines and polyamines and prepared the corresponding DPG salts. The structures of the DPG salts are depicted in FIG. 20 along with their 1-octanol/water and 1-octanol/serum partition coefficients.

The different salts were then tested for $P_{50}$ shift measurements on whole blood. The results of these biological tests are summarized in Table 3.

TABLE 3

Whole blood $P_{50}$ measurements in the presence of various DPG salts.

| NAME EFFECTOR (EFF) | | P50 CONTROL mmHg WB | P50 mmHg EFF:WB | pH/37° C. P50 Measured HemoxAnalyzer Hemox+ EFF:washed RBC | Osmolality of Effector (220–240) mOsM | RATIOS * EFF:WB | NAME EFFECTOR (EFF) | |
|---|---|---|---|---|---|---|---|---|
| SV172 | | | | | | | SV172 | |
| | WB | 36 | Lyses | 7.2–7.3 | 109 | 1:0.375 | | WB |

TABLE 3-continued

Whole blood P$_{50}$ measurements in the presence of various DPG salts.

| NAME EFFECTOR (EFF) | P50 CONTROL mmHg WB | P50 mmHg EFF:WB | pH/37° C. P50 Measured HemoxAnalyzer Hemox+ EFF:washed RBC | Osmolality of Effector (220–240) mOsM | RATIOS * EFF:WB | NAME EFFECTOR (EFF) |
|---|---|---|---|---|---|---|
|  | WB | 36 | 36.0 | 7.2–7.3 | 311 | 1:0.375 |  | WB |
| SV164 |  |  |  |  |  |  | SV164 |
|  | WB | 36 | 46.8 | 7.2–7.3 | 126 | 1:0.375 |  | WB |
|  | WB | 36 | 36.0 | 7.2–7.3 | 337 | 1:0.375 |  | WB |
| SV174 |  |  |  |  |  |  | SV174 |
|  | WB | 36 | 46.8 | 7.2–7.3 | 85 | 1:0.375 |  | WB |
|  | WB | 36 | 36.0 | 7.2–7.3 | 289 | 1:0.375 |  | WB |
|  | WB | 36 | 36.0 | 7.2–7.3 | 85 | 1:1.5 |  | WB |
| SV168 |  | Insoluble |  |  |  |  | SV168 |
| SV216 |  | Insoluble |  |  |  |  | SV216 |

The results obtained with DPG salts are in good agreement with those discussed above for the IHP ammonium salts. The cyclooctylammonium salt SV164 displayed the best properties with regard to partitioning in an octanolic phase and transport across the red blood cell membrane. Once again, acyclic aliphatic (poly)amines gave insoluble polyphosphaste salts in aqueous media.

VI. Methods of the Invention

In certain embodiments, the method of the present invention comprises the step of administering to a subject red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject experiencing ischemia red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject experiencing ischemia red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject experiencing cardiac arrhythmia red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject experiencing cardiac arrhythmia red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject experiencing a heart attack red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject experiencing a heart attack red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject experiencing a stroke red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject experiencing a stroke red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject experiencing hypoxia red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject experiencing hypoxia red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject afflicted with sickle cell anemia red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject afflicted with sickle cell anemia red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject suffering from hypotension red blood cells or whole blood that has previously been treated ex vivo with a compound or composition of the present invention, and wherein the red blood cells or whole blood has been subsequently suitably purified such that when said red blood cells or whole blood is administered to a subject it is nontoxic to said subject.

In certain embodiments, the method of the present invention comprises the step of administering to a subject suffering from hypotension red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject suffering from arteriosclerosis red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject suffering from arteriosclerosis red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject suffering from altitude sickness red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject suffering from altitude sickness red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of administering to a subject suffering from diabetes red blood cells or whole blood that has previously been treated ex vivo with a compound or composition of the present invention, and wherein said red blood cells or whole blood has been subsequently suitably purified such that when said red blood cells or whole blood is administered to a subject it is nontoxic to said subject.

In certain embodiments, the method of the present invention comprises the step of administering to a subject suffering from diabetes red blood cells or whole blood that has previously been treated ex vivo with a compound or composition of the present invention, wherein said red blood cells or whole blood has been subsequently suitably purified such that when said red blood cells or whole blood is administered to a subject it is nontoxic to said subject, and wherein said administration is intravenous.

In certain embodiments, the method of the present invention comprises the step of adding to mammalian blood a compound or composition of the present invention.

In certain embodiments, the method of the present invention comprises the step of adding to plasma comprising mammalian erythrocytes a compound or composition of the present invention.

IX. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. A natural requirement for any pharmaceutically acceptable composition is that it comprise a nontoxic compound of the present invention. We are aware that many of the modem drugs of great benefit have started out as toxic substances. Ongoing research in our laboratories is directed towards nontoxic compounds of ammonium salts and anionic allosteric effectors. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals A without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

X. Administration of the Compounds of the Present Invention

In another aspect, the current invention provides methods of administering to a subject pharmaceutical compositions comprised of a nontoxic ammonium salt of an anionic allosteric effector. Many techniques currently exist for delivering drugs or other medicaments to body tissue. These include, among possible others, oral administration, injection directly into body tissue such as through an intramuscular injection or the like, topical or transcutaneous administration where the drug is passively absorbed, or caused to pass, into or across the skin or other surface tissue and intravenous administration which involves introducing a selected drug directly into the blood stream. Techniques and formulations generally may be found in Remmington's Pharmaceutical Sciences, Meade Publishing Co., Easton, Pa.

Exemplification

The invention now being generally described, it will be more readily understood by reference to the following examples, which are included merely for purposes of illustration of certain aspects and embodiments of the present invention, and are not intended to limit the invention.

Physical Chemistry

Human serum was purchased at the "Centre de Transfusion Sanguine de Strasbourg". Artificial serum was based on blood composition: $[Na^+]=140$ mM, $[Mg^{2+}]=1$ mM, $[K^+]=5$ mM, $[Ca^{2+}]=1$ mM, $[Cl^-]=106$ mM, $[PO_4^{3-}]=1$ mM, $[SO_4^{2-}]=0.5$ mM, $[CO_3^{2-}]=30$ mM, $[Br^-]=0.5$ mM, bovine serum albumin (fraction V, >98%) 30 g.l$^{-1}$, pH=7.41.

Partition coefficients. IHP derivatives were dissolved in 1 ml of aqueous phase at a concentration of 30 mM in an eppendorf. 1 ml of 1-octanol was then added and each sample was shaken at 36 rpm during 12 hours. The equilibrated biphasic solutions were centrifuged for 2 hours at 3000 rpm. 350 µl of the octanolic phase was first taken off with a syringe and put directly in the NMR tube. 350 µl of the aqueous phase was then taken off. $^{31}$P-NMR spectra were performed on a Bruker AC-300 apparatus. An external standard (triphenylphosphine oxide, 60 mM in $d_6$-DMSO) was placed inside the NMR tubes to allow both the locking process of the apparatus and an accurate integration of IHP peaks. Partition coefficients were determined as the ratio of IHP integrations, relative to the external standard, in the octanol and aqueous phases. The detection limits of this technique do not allow partition coefficients measurements below $10^{-3}$.

General Procedures

IHP polyammoniums Synthesis. A 100 mM IHP dodecasodium salt solution was applied on a cation exchange column (dowex WX8-200, $H^+$ form) and eluted with distilled water. The fractions containing the perprotonated IHP were collected and poured onto an ethanolic solution of the desired amine. The solution was then concentrated in vacuo, redissolved in ethanol or in a 1/1 toluene/EtOH mixture and reconcentrated. The IHP-ammonium salts were characterized by $^1$H- and $^{31}$P-NMR.

IHP-, DPG-ammonium salts Syntheses

SV44 Inositol hexaphosphate, hepta 3-hydroxy-quinuclidinium salt

The general procedure was applied from commercial IHP, dodecasodium form, and 3-hydroxy-quinuclidine. White solid.

$^1$H-NMR (200 MHz, D$_2$O) δ4.89 (d, J=10.4 Hz, 1H), 4.42 (q, J=10.4 Hz, 2H), 4.17 (m, 10H), 3.62 (m, 7H), 3.25 (m, 35H), 2.18 (m, 35H).

$^{31}$P-NMR (121 MHz, D$_2$O) δ1.88 (1P), 1.26 (2P), 0.67 (2P), 0.25 (1P).

SV46 Inositol hexaphosphate, nona piperidinium salt

The general procedure was applied from commercial IBP, dodecasodium form, and piperidine. White solid.

$^1$H-NMR (200 MHz, D$_2$O) δ4.25 (q, J=9.9 Hz, 2H), 3.98 (m, 3H), 3.01 (m, 36H), 1.58 (m, 54H).

$^{31}$P-NMR (121 MHz, D$_2$O) δ2.55 (1P), 1.59 (2P), 1.34 (2P), 1.17 (1P).

SV48 Inositol hexaphosphate, nona phenylalanine-methyl-ester

The general procedure was applied from commercial IHP, dodecasodium form, and phenylalanine methyl-ester. White solid.

$^1$H-NMR (200 MHz, D$_2$O) δ7.31 (m, 45H), 4.88 (d, J=10.0 Hz, 1H), 4.41 (q, J=10.0 Hz, 2H), 4.21 (m, 12H), 3.71 (m, 27H), 1.17 (bd, J=10.0 Hz, 18H).

$^{31}$P-NMR (121 MHz, D$_2$O) δ2.18 (1P), 1.51 (2P), 1.00 (2P), 0.59 (1P).

SV51 Inositol hexaphosphate, hexa dihydro-quinolidinium salt

The general procedure was applied from commercial IHP, dodecasodium form, and dihydro-quinolidine. White solid.

$^1$H-NMR (200 MHz, D$_2$O) δ7.51 (m, 24H), 4.83 (m, 7H), 4.48 (q, J=9.8 Hz, 2H), 4.21 (m, 3H), 3.01 (m, 12H), 2.55 (m, 6H), 2.13 (m, 6H).

$^{31}$P-NMR (121 MHz, D$_2$O) δ2.18 (1P), 1.51 (2P), 0.92 (2P), 0.54 (1P).

SV52 Inositol hexaphosphate, hepta 2-norbornyl-ammonium salt

The general procedure was applied from commercial IHP, dodecasodium form, and 2-norbornylaminer. White solid.

$^1$H-NMR (200 MHz, D$_2$O) δ4.85 (d, J=9.9 Hz,1H), 4.36 (q, J=9.9 Hz, 2H), 4.08 (m, 3H), 3.48 (m, 7H), 2.31 (m, 14H), 1.97 (bt, J=11.0 Hz,1H), 1.28 (m, 49H).

$^{31}$P-NMR (121 MHz, D$_2$O) δ2.67 (1P), 1.84 (2P), 1.46 (2P), 1.34 (1P).

SV53 Inositol hexaphosphate, nona decahydroquinolinium salt

The general procedure was applied from commercial IHP, dodecasodium form, and decahydro-quinoline. White solid.

$^1$H-NMR (300 MHz, D$_2$O) δ4.31 (q, J=9.7 Hz, 2H), 3.4–2.8 (m, 27H), 1.9–1.0 (m, 117H).

$^{31}$P-NMR (121 MHz, D$_2$O) δ2.84 (1P), 2.01 (3P), 1.59 (2P).

SV55 Inositol hexaphosphate, hepta phenylalanine-ethyl-ester

The general procedure was applied from commercial IHP, dodecasodium form, and phenylalanine ethyl-ester. White solid.

$^1$H-NMR (300 MHz, D$_2$O) δ7.22 (m, 35H), 4.33 (q, J=9.6 Hz, 2H), 4.21 (m, 24H), 3.07 (m, 7H), 1.07 (t, J=7.1 Hz, 21 H).

$^{31}$P-NMR (121 MHz, D$_2$O) δ2.63 (1P), 1.63 (5P).

SV57 Inositol hexaphosphate, octa isoleucine-tbuthyl-ester

The general procedure was applied from commercial IHP, dodecasodium form, and isoleucine tBu-ester. White solid.

$^1$H-NMR (300 MHz, D$_2$O) δ4.35 (q, J=9.7 Hz, 2H), 4.09 (m, 3H), 3.84 (d, J=4.0 Hz, 8H), 1.91 (bs, 8H), 1.5–0.8 (m, 120H).

$^{31}$P-NMR (121 MHz, D$_2$O) δ1.88 (1P), 1.30 (2P), 0.75 (2P), 0.25 (1P).

SV58 Inositol hexaphosphate, dodeca diisopropylammonium salt

The general procedure was applied from commercial IHP, dodecasodium form, and diisopropylamine. White solid.

$^1$H-NMR (300 MHz, D$_2$O) δ4.33 (q, J=9.9 Hz, 2H), 4.05 (m, 3H), 3.38 (h, J=4.6 Hz, 12H), 1.18 (d, J=4.6 Hz, 120H).

$^{31}$P-NMR (121 MHz, D$_2$O) δ2.09 (1P), 1.38 (2P), 0.75 (2P), 0.33 (1P).

SV59 Inositol hexaphosphate, octa proline-t-buthyl-ester

The general procedure was applied from commercial IHP, dodecasodium form, and proline tBu-ester. White solid.

$^1$H-NMR (300 MHz, D$_2$O) δ4.35 (m, 10H), 4.02 (m, 3H), 3.29 (m, 16H), 2.26 (m, 8H), 1.95 (m, 24H), 1.36 (m, 72H).

$^{31}$P-NMR (121 MHz, D$_2$O) δ2.21 (1P), 1.42 (2P), 0.92 (2P), 0.54 (1P).

SV68 Inositol hexaphosphate, hepta tyrosine-ethyl-ester salt

The general procedure for IHP ammonium salt preparation was applied from IHP dodecasodium form and the commercially available amine.

$^1$H NMR (300 MHz; D$_2$O) δ7.06 (d, J=8.04 Hz, 20H), 6.77 (d, J=7.70 Hz, 20H), 4.37 (q, J=9.8 Hz, 2H), 4.41 (m, 33H), 4.22 (m, 7H), 3.96 (m, 14H), 3.44 (bs, 14H), 1.04 (t, J=7.3 Hz, 6 11H).

$^{31}$P NMR (121 MHz; D$_2$O) δ3.00 (1P), 2.75 (2P), 2.58 (2P), 1.50 (1P).

SV74 Inositol hexaphosphate, undeca-adamantylammonium salt

The general procedure for IHP ammonium salt preparation was applied from IHP dodecasodium form and the commercially available amine.

$^1$H NMR (300 MHz; CD$_3$OD/CDCl$_3$ 3/1) δ4.53 (q, J=9.87 Hz, 2H), 4.14 (m, 3H), 3.41 (bs, 11H), 1.9–0.9 (m, 154H);

$^{31}$P NMR (121 MHz; CD$_3$OD/CDCl$_3$ 3/1) δ2.72 (1P), 2.30 (2P), 1.84 (3P).

SV75 Inositol hexaphosphate, nona-cycloheptylammonium salt

The general procedure for IHP ammonium salt preparation was applied from IHP dodecasodium form and the commercially available amine.

$^1$H NMR (300 MHz; D$_2$O) δ4.34 (q, J=9.95 Hz, 2H), 4.01 (m, 3H), 3.26 (qi, J=5.13 Hz, 9H), 1.95 (m, 18H), 1.70–1.35 (m, 90H);

$^{31}$P NMR (121 MHz; D$_2$O) δ3.22, 2.76, 2.47, 2.09.

SV78 Inositol hexaphosphate, undeca-cyclopentylammonium salt

The general procedure for IHP ammonium salt preparation was applied from IHP dodecasodium form and the commercially available amine.

$^1$H NMR (300 MHz; D$_2$O) δ4.29 (q, J=9.30 Hz, 2H), 3.98 (m, 3H), 3.53 (bs, 11H), 1.9–0.9 (m, 88H);

$^{31}$P NMR (121 MHz; D$_2$O) δ2.72 (1P), 2.30 (2P), 1.84 (3P).

SV81 Inositol hexaphosphate, undeca-cyclohexylammonium salt

The general procedure for IHP ammonium salt preparation was applied from IHP dodecasodium form and the commercially available amine.

$^1$H NMR (300 MHz; D$_2$O) δ4.26 (q, J=9.60 Hz, 2H), 3.94 (m, 3H), 2.91 (bs, 11H), 1.9–0.9 (m, 110H);

$^{31}$P NMR (121 MHz; D$_2$O) δ3.18, 2.68, 2.39, 2.09.

SV92 Inositol hexaphosphate, penta (±)-(trans)-1,2-cyclohexyldiammonium salt

The general procedure for IHP ammonium salt preparation was applied from IHP dodecasodium form and the commercially available amine.

$^1$H NMR (300 MHz; D$_2$O) δ4.81 (m, 1H), 4.31 (q, J=9.40 Hz, 2H), 4.09 (m, 3H), 3.57 (m, 2.5H), 3.22 (m, 5H), 2.93 (m, 2.5H), 2.08 (bd, 5 H), 1.80–1.25 (m, 30H);

$^{31}$P NMR (121 MHz; D$_2$O) δ3.43 (2P), 2.39 (1P), 2.09 (2P), 1.97 (1P).

SV94 Inositol hexaphosphate, penta cyclohexyl-(1,3-bismethylammonium) salt

The general procedure was applied from commercial IHP, dodecasodium form, and 1,3-bis-aminomethyl-cyclohexane (mixture of isomers). White solid.

$^1$H-NMR (300 MHz, D$_2$O) δ4.37 (m, 3H), 4.18 (bd, 0.5H), 2.82 (m, 13H), 2.66 (m, 5H), 1.93 (m, 5H), 1.8–1.1 (m, 32H), 0.89 (q, J=12.2 Hz, 7H), 0.66 (q, J=12.2 Hz, 3H).

$^{31}$P-NMR (121 MHz, D$_2$O) δ5.69 (2P), 4.32 (3P), 3.56 (1P).

SV97 Inositol hexaphosphate, nona N-cyclohexyl-piperidinium salt

The general procedure was applied from commercial IHP, dodecasodium form, and N-cyclohexyl-piperidine. White solid.

$^1$H-NMR (300 MHz, D$_2$O) δ4.91 (d, J=10.1 Hz, 1H), 4.35 (q, J=10.0 Hz, 2H), 4.09 (bq, J=9.3 Hz, 3H), 3.20 (s, 36H), 3.02 (s, 36H), 2.67 (m, 9H), 1.93 (m, 18H), 1.59 (bd, 9H), 1.3–0.9 (m, 45H).

$^{31}$P-NMR (121 MHz, D$_2$O) δ2.63 (1P), 2.26 (2P), 2.05 (1P), 1.76 (1P).

SV99 Inositol hexaphosphate, hexa N,N-dimethyl-cyclohexylammonium salt

The general procedure was applied from commercial IHP, dodecasodium form, and N,N-dimethyl-cyclohexylamine. White solid.

$^1$H-NMR (300 MHz, D$_2$O) δ4.84 (bd, 1H), 4.41 (q, J=9.9 Hz, 2H), 4.14 (m, 3H), 3.11 (t, J=11.4 Hz, 6H), 2.80 (s, 36H), 1.95 (bd, 12H), 1.81 (bd, 12H), 1.58 (bd, 6H), 1.3–1.0 (m, 36H).

$^{31}$P-NMR (121 MHz, D$_2$O) δ1.55 (1P), 1.09 (2P), 0.63 (2P), 0.13 (1P).

SV72 Inositol hexaphosphate, penta-(N,N'-dibenzyl)-ethylenediammonium salt

The general procedure for IHP ammonium salt preparation was applied from IHP dodecasodium form and the commercially available amine.

$^1$H NMR (200 MHz; CD$_3$OD/CDCl$_3$ 3/1) δ7.45–7.21 (m, 80H), 4.99 (d, J=10.0 Hz, 1H), 4.79 (s, 40H), 4.44–4.21 (m, 5H), 3.91 (bs, 32H), 2.98 (bs, 32H);

$^{31}$P NMR (121 MHz; CD$_3$OD/CDCl$_3$ 3/1) δ3.00 (1P), 2.75 (2P), 2.58 (2P), 1.50 (1P).

SV89 Inositol hexaphosphate, octa menthyl-1,8-diammonium salt

The general procedure was applied from commercial IHP, dodecasodium form, and 1,8-diamino-menthane. White solid.

$^1$H-NMR (200 MHz, D$_2$O) δ4.45 (q, J=9.7 Hz, 2H), 3.97 (m, 3H), 1.9–0.8 (m, 150H).

$^{31}$P-NMR (121 MHz, D$_2$O) δ4.52 (2P), 2.80 (1P), 2.68 (1P), 2.51 (2P).

SV94 Inositol hexaphosphate, penta cyclohexyl-(1,3-bismethylammonium) salt

The general procedure was applied from commercial IHP, dodecasodium form, and 1,3-bis-aminomethyl-cyclohexane (mixture of isomers). White solid.

$^1$H-NMR (300 MHz, D$_2$O) δ4.37 (m, 3H), 4.18 (bd, 0.5H), 2.82 (m, 13H), 2.66 (m, 5H), 1.93 (m, 5H), 1.8–1.1 (m, 32H), 0.89 (q, J=12.2 Hz, 7H), 0.66 (q, J=12.2 Hz, 3H).

$^{31}$P-NMR (121 MHz, D$_2$O) δ5.69 (2P), 4.32 (3P), 3.56 (1P).

SV95 Inositol hexaphosphate, penta (±)-(1,2-trans-diphenyl)-ethylenediammonium salt The general procedure was applied from commercial IHP, dodecasodium form, and 1,2-trans-diphenyl-ethylenediamine. White solid.

$^1$H-NMR (300 MHz, D$_2$O) δ7.25 (m, 50H), 5.03 (bd, 1H), 4.81 (s, partially overlapped with the D$_2$O peak), 4.49 (q, J=10.0 Hz, 2H), 4.25 (m, 3H).

SV97 Inositol hexaphosphate, nona N-cyclohexyl-piperidinium salt

The general procedure was applied from commercial IHP, dodecasodium form, and N-cyclohexyl-piperidine. White solid.

$^1$H-NMR (300 MHz, D$_2$O) δ4.91 (d, J=10.1 Hz, 1H), 4.35 (q, J=10.0 Hz, 2H), 4.09 (bq, J=9.3 Hz, 3H), 3.20 (s, 36H), 3.02 (s, 36H), 2.67 (m, 9H), 1.93 (m, 18H), 1.59 (bd, 9H), 1.3–0.9 (m, 45H).

$^{31}$P-NMR (121 MHz, D$_2$O) δ2.63 (1P), 2.26 (2P), 2.05 (1P), 1.76 (1P).

SV101 Inositol hexaphosphate, bis (N$^1$,N$^3$-cyclohexyl)-dipropylenetriammonium salt The general procedure was applied from commercial IHP, dodecasodium form, and triamine SV91. White solid.

$^1$H-NMR (300 MHz, D$_2$O) δ4.90 (bm, 1H), 4.35 (bm, 2H), 4.15 (bm, 3H), 3.06 (t, 16H), 2.07 (m, 16H), 1.77 (bs, 8H), 1.59 (bs, 4H), 1.3–1.0 (m, 24H).

$^{31}$P-NMR (121 MHz, D$_2$O) δ2.18 (1P), 1.38 (2P), 0.88 (3P).

SV102 Inositol hexaphosphate, tris tri-(N-cyclohexyl-2-amino-ethyl)-ammonium salt The general procedure was applied from commercial IHP, dodecasodium form, and tetramine SV98. White solid.

$^1$H-NMR (300 MHz, D$_2$O) δ4.81 (bd, J=9.9 Hz, 1H), 4.34 (q, J=9.9 Hz, 2H), 4.01 (m, 3H), 3.1–2.7 (m, 45H), 1.99 (m, 15H), 1.65–1.5 (m, 30H), 1.4–1.0 (m, 45H).

$^{31}$P-NMR (121 MHz, D$_2$O) δ2.43 (1P), 2.30 (1P), 2.13 (2P), 1.80 (2P).

SV106 Inositol hexaphosphate, tetra N,N'-di-(3-(N-cyclohexyl-amino)-propyl)-piperazinium salt The general procedure was applied from commercial IHP, dodecasodium form, and tetramine SV103. White solid.

$^1$H-NMR (300 MHz, D$_2$O) δ4.90 (bd, J=9.8 Hz, 1H), 4.34 (q, J=9.8 Hz, 2H), 4.03 (m, 3H), 2.98 (bt, J=7.1 Hz, 24H), 2.60 (bs, 24H), 2.50 (bt, J=7.1 Hz, 24H), 1.99 (bs, 16H), 1.80 (m, 32H), 1.60 (m, 8H), 1.40–1.05 (m, 44H).

SV137 Inositol hexaphosphate, tris tri-(N-cycloheptyl-2-amino-ethyl)-ammonium salt The general procedure was applied from commercial IHP, dodecasodium form, and tetramine SV127. White solid.

$^1$H-NMR (300 MHz, D$_2$O) δ4.81 (bd, J=9.3 Hz, 1H), 4.39 (q, J=9.3 Hz, 2H), 4.12 (m, 3H), 3.25 (m, 6H), 3.22 (m, 10H), 2.94 (m, 10H), 2.02 (m, 12H), 1.70–1.40 (m, 60H).

$^{31}$P-NMR (121 MHz, D$_2$O) δ2.36 (1P), 1.23 (2P), 0.67 (2P), 0.44 (1P).

SV141 Inositol hexaphosphate, tri N,N'-di-(3-(N-cyclooctyl-amino)-propyl)-piperazinium salt The general procedure was applied from commercial IHP, dodecasodium form, and tetramine SV129. White solid.

$^1$H-NMR (300 MHz, D$_2$O) δ4.89 (bd, J=10.4 Hz, 1H), 4.30 (q, J=9.7 Hz, 2H), 4.03 (m, 3H), 3.25 (m, 8H), 2.99 (bt, J=7.1 Hz, 14H), 2.65 (bs, 16H), 2.45 (bt, J=7.1 Hz, 14H), 1.96 (m, 28H), 1.80–1.20 (m, 84H).

$^{31}$P-NMR (121 MHz, D$_2$O) δ7.87 (1P), 7.72 (2P), 7.13 (1P), 6.60 (2P).

SV202 Inositol hexaphosphate, bis N,N',N'',N'''-tetrahexyl-cyclam salt

The general procedure was applied from commercial IHP, dodecasodium form, and tetramine SV198. White solid.

$^1$H-NMR (300 MHz, CD$_3$OD/CDCl$_3$ 1/1) δ4.96 (bd, J=11.1 Hz, 11H), 4.25 (t, J=9.3 Hz, 1H), 4.15 (t, J=9.3 Hz, 2H), 3.4–2.6 (bm, 44H), 2.17 (s, 4H), 1.54 (m, 12H), 1.29 (m,60H), 0.86 (t, J=6.0 Hz, 24H).

$^{31}$P-NMR (121 MHz, CD$_3$OD/CDCl$_3$ 1/1) δ1.69 (2P), 0.93 (1P), 0.51 (2P), 0.25 (1P).

EXAMPLE 1

This example shows that ammonium salts of Inositol Hexaphosphate (IHP) improve the dissociation of oxygen from hemoglobin following incubation with whole blood.

A. Effectors

See FIGS. 1–3.

B. Blood Preparations

Whole blood was collected from one subject. The blood was stored in a Vacutainer with Solution A (ACD) and stored at 4–8° C.

To isolate red blood cells, whole blood (3 mL) was placed on top of test tube containing 9 mL of Histopaque 1119 (Sigma Diagnostics Inc.) and 1 mL of Saline buffer. Following centrifugation the supernatant and buffy coat were removed and the pellet containing RBCs were washed three times in 10 mL HBS.

C. Buffers

HBS=HEPES Buffered Saline,

HBS was used as the standard buffer for experiments. HBS 7.42 (r.t.) was ideal to keep pH of experiments at 7.28–7.32 (37° C.).

20 mM HEPES 130 mM Sodium Chloride

HEPES, (N-[2-hydroxyethyl]piperazine-N'-[2-ethanesulfonic acid])

$C_8H_{18}N_2O_4S$

F.W.=238.3 pK$_a$=7.5 pH: 6.8–8.2

CAS# 7365-45-9

HBS+ HBS

20 μL Bovine Serum Albumin (BSA) per 5 mL HBS (TCS Medical Products Company)

15 μL Antifoaming per 5 mL HBS (TCS Medical Products Company)

pH: 7.2–7.4

Osmolarity: 290–320 mOsM

HBS·BSA mL HBS Plus 20 μL BSA
saline, 0.9% Sodium Chlorida, Injection USP
Each 100 mL contains:

| | |
|---|---|
| 900 mg | NaCl |
| 154 mEq/L | Sodium |
| 154 mEq/L | Chloride |
| pH: | 5.0 |
| | Osmolarity: 308 mOsM |

BIS-TRIS buffered saline, (bis[2-Hydroxyethyl]minotris [hydroxymethyl]methane), (Sigma).

20 mM Bis-Tris
140 mM Sodium Chloride
pH: 7.45
Osmolarity: 294 mOsM

D. Procedures

Preparation of Effector Stock: Effector stock was prepared at 100–120 mM (Molal solution) using water or Bis-Tris Buffer. Effector characteristics prior to incubation were:

| | |
|---|---|
| Concentration: | 30 mM |
| Osmolarity: | 170–340 mOsM |
| pH: | 7.1–7.4 (at 37° C.) |

Incubation: Whole blood (75–300 μL) was incubated with 200 μL of effector at 37° C. for 5–10 min. (see Summary of Results below).

Washes: After incubation of whole blood with/without effector, blood cells were washed four times with Saline buffer or HBS (BSA) by centrifugal pelleting to remove exogenous effector and to evaluate hemolysis. After final centrifugation, pellet was not resuspended.

Blood Oxygen Dissociation Reading: Blood Oxygen Dissociation of samples were determined using a Hemox Analizer Model B (TCS Medical Products Company, New Hope, Pa.). The sample chamger contained:

Control:
  2.5–3.0 mL of HBS+
  25 μL Whole blood
Effector evaluation:
  2.5–3.0 mL of HBS+
  10–20 μL Pelleted Blood Cells incubated with Effector All readings were made at 36.7–37.2° C. and at pH 7.28–7.32. The $P_{50}$s were calculated from the Dissociation Curves compared to same day control $P_{50}$.

Example 1

Summary of Results

| | $P_{50}$ of Whole Blood Pre-Incubated with Effector (Low Osmolarity) (All incubations and measurements at 37 +/− 0.2 C.) | | | | | | | |
|---|---|---|---|---|---|---|---|---|
| EFFECTOR | $P_{50}$ CONTROL WB mmHg | $P_{50}$ EFF:WB mmHg | CONC. EFF mM | CONC EFF:WB mM | OSMOL. EFF mOsM | pH EFF. | pH EFF:WB | Volume Ratio EFF:WB |
| ICP6 | 27.5 | 39 | 30 | 22 | 220 | | 7.23 | 1:0.375 |
| NH4-IHP | 26 | 54 | 30 | 22 | 106 | | 7.29 | 1:0.375 |
| | 28.5 | 43 | 30 | 22 | 106 | | 7.28 | 1:0.375 |
| | 30 | 53.5 | 30 | 22 | 94 | | 7.43 | 1:0.375 |
| SV73 | 38 | 57 | 30 | 22 | 68 | | 7.54 | 1:0.375 |

WB = whole blood;
EFF = allosteric effector;
ICP6 = nona cyclohexylammonium tri sodium inositol hexaphosphate; SV73, see FIG. 3.
The control value for whole blood's $P_{50}$ varies due to aging of the blood. Aging is accompanied by the degradation of natural allosteric effectors by native phosphotases.

See also FIGS. 4–9.

E. Conclusion

Ammonium Salts of IHP increase the $P_{50}$ of whole blood in comparison to the sodium salts of these two allosteric effectors at osmolarities less than 280 mOsM.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are encompassed by the following claims.

We claim:

1. A composition represented by structure 1:

wherein
nC$^+$ represents nona-cyclohexylammonium-tri-sodium, bis-dicyclohexylammonium-deca-sodium, octa-dicyclohexylammonium, hepta-1-aza-3-hydroxyl-bicyclo[2.2.2]cyclooctanium, dodeca-1-aza-3-hydroxyl-bicyclo[2.2.2]cyclooctanium, nona-piperidinium, penta-H$_3$N-Phe-OMe, nona-H$_3$N-Phe-OMe, hexa-1-indanylammonium, hepta-2-norbornylammonium, nona-decahydroquinolinium, hepta-H$_3$N-Phe-OEt, hexa-H$_3$N-Phe-OEt, octa-H$_3$N-sec-Leu-Ot-Bu, dodeca-diisopropylammonium, octa-H$_3$N-Pro-Ot-Bu, deca-H$_3$N-Tyr-OEt, tetra-cyclohexyl-1,2-bis-ammonium, nona-cycloheptylammonium, undeca-cyclopentylammonium, or undeca-cyclohexylammonium, penta-(N,N'-dibenzyl)-ethylenediammonium, octa menthyl-1,8-diammonium, penta cyclohexyl-(1,3-bismethylammonium), penta (±)-(1,2-transdiphenyl)-ethylenediammonium, nona N-cyclohexyl-piperidinium, bis (N$^1$,N$^3$-cyclohexyl)-dipropylenetriammonium, tris tri-(N-cyclohexyl-2-amino-ethyl)-ammonium, tetra N,N'-di-(3-(N-cyclohexyl-amino)-propyl)-piperazinium, tris tri-(N-cycloheptyl-2-amino-ethyl)-ammonium, tri N,N'-di-(3-(N-cyclooctyl-amino)-propyl)-piperazinium, or bis N,N',N'',N'''-tetrahexyl-cyclam; and A$^{n-}$ represents a conjugate base of inositol hexaphosphate, wherein n equals the number of cations comprised by nC$^+$.

2. The compound of claim 1, wherein nC$^{30}$ represents nona-cyclohexylammonium-tri-sodium, bis-dicyclohexylammonium-deca-sodium, octa-dicyclohexylammonium, hepta-1-aza-3-hydroxyl-bicyclo[2.2.2]cyclooctanium, dodeca-1-aza-3-hydroxyl-bicyclo[2.2.2]cyclooctanium, nona-piperidinium, penta-H$_3$N-Phe-OMe, nona-H$_3$N-Phe-OMe, hepta-2-norbornylammonium, nona-decahydroquinolinium, hepta-H$_3$N-Phe-OEt, hexa-H$_3$N-Phe-OEt, dodeca-diisopropylammonium, octa-H$_3$N-Pro-Ot-Bu, deca-H$_3$N-Tyr-OEt, tetra-cyclohexyl-1,2-bis-ammonium, nona-cycloheptylammonium, undeca-cyclopentylammonium, undeca-cyclohexylammonium, octa menthyl-1,8-diammonium, penta cyclohexyl-(1,3-bismethylammonium), nona N-cyclohexyl-piperidinium, bis (N$^1$,N$^3$-cyclohexyl)-dipropylenetriammonium, tris tri-(N-cyclohexyl-2-amino-ethyl)-ammonium, tetra N,N'-di-(3-(N-cyclohexyl-amino)-propyl)-piperazinium, tris tri-(N-cycloheptyl-2-amino-ethyl)-ammonium, or tris N,N'-di-(3-(N-cyclooctyl-amino)-propyl)-piperazinium.

3. The compound of claim 1, wherein nC$^{30}$ represents nona-cyclohexylammonium-tri-sodium, octa-dicyclohexylammonium, nona-decahydroquinolinium, dodeca-diisopropylammonium, octa-H$_3$N-Pro-Ot-Bu, nona-cycloheptylammonium, or undeca-cyclohexylammonium.

4. The compound of claim 1, wherein nC$^{30}$ represents nona-decahydroquinolinium, dodeca-diisopropylammonium, octa-H$_3$N-Pro-Ot-Bu, nona-cycloheptylammonium, or undeca-cyclohexylammonium.

5. The compound of claim 1, wherein nC$^{30}$ represents nona-cycloheptylammonium or undeca-cyclohexylammonium.

6. The compound of claim 1, wherein nC$^{30}$ represents nona-cycloheptylammonium.

7. The compound of claim 1, wherein nC$^{30}$ represents undeca-cyclohexylammonium.

* * * * *